US010737000B2

(12) United States Patent
Braga et al.

(10) Patent No.: US 10,737,000 B2
(45) Date of Patent: Aug. 11, 2020

(54) SENSOR WITH ELECTRICAL CONTACT PROTECTION FOR USE IN FLUID COLLECTION CANISTER AND NEGATIVE PRESSURE WOUND THERAPY SYSTEMS INCLUDING SAME

(71) Applicant: SMITH & NEPHEW, INC., Memphis, TN (US)

(72) Inventors: Richard M. Braga, North Easton, MA (US); David R. Swisher, St. Charles, MO (US)

(73) Assignee: Smith & Nephew, Inc., Memphis, TN (US)

( * ) Notice: Subject to any disclaimer, the term of this patent is extended or adjusted under 35 U.S.C. 154(b) by 256 days.

(21) Appl. No.: 15/791,245

(22) Filed: Oct. 23, 2017

(65) Prior Publication Data
US 2018/0104387 A1     Apr. 19, 2018

Related U.S. Application Data

(63) Continuation of application No. 15/219,045, filed on Jul. 25, 2016, now Pat. No. 9,801,984, which is a
(Continued)

(51) Int. Cl.
*A61M 5/00* (2006.01)
*A61M 1/00* (2006.01)
(Continued)

(52) U.S. Cl.
CPC ........ *A61M 1/0025* (2014.02); *A61M 1/0001* (2013.01); *A61M 1/0031* (2013.01);
(Continued)

(58) Field of Classification Search
CPC .......... A61M 5/00; A61M 5/31; A61M 37/00; A61M 25/18; A61M 1/00; A61M 27/00;
(Continued)

(56) References Cited

U.S. PATENT DOCUMENTS 730,062 A    6/1903   Widmer
2,468,445 A  4/1949   Hurst
(Continued)

FOREIGN PATENT DOCUMENTS

CA    2 732 514    2/2010
CN     2623320     7/2004
(Continued)

OTHER PUBLICATIONS

US 6,216,701 B1, 04/2001, Heaton et al. (withdrawn)
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

A sensor for use in a canister for fluid collection, the canister having a canister top and defining a fluid collection chamber. The sensor includes a first electrode and a second electrode. The first electrode includes a first portion and a second portion, wherein the first portion of the first electrode is supported by the canister top, and the second portion of the first electrode is configured to extend into the fluid collection chamber. The second electrode includes a first portion and a second portion, wherein the first portion of the second electrode is supported by the canister top, and the second portion of the second electrode is configured to extend into the fluid collection chamber. The sensor also includes an electric circuit configured to detect an electrical property associated with the first and second electrodes.

13 Claims, 9 Drawing Sheets

Related U.S. Application Data continuation of application No. 14/473,063, filed on Aug. 29, 2014, now Pat. No. 9,415,145, which is a continuation of application No. 12/471,789, filed on May 26, 2009, now Pat. No. 8,827,983.

(60) Provisional application No. 61/090,782, filed on Aug. 21, 2008.

(51) Int. Cl.

| | | |
|---|---|---|
| *G01F 23/02* | (2006.01) | |
| *G01F 23/24* | (2006.01) | |
| *G01F 23/26* | (2006.01) | |
| *A61M 5/31* | (2006.01) | |
| *A61M 37/00* | (2006.01) | |
| *A61M 25/18* | (2006.01) | |
| *A61M 27/00* | (2006.01) | |

(52) U.S. Cl.
CPC ........ *A61M 1/0049* (2013.01); *A61M 1/0052* (2014.02); *A61M 1/0088* (2013.01); *G01F 23/02* (2013.01); *G01F 23/241* (2013.01); *G01F 23/268* (2013.01); *A61M 2205/18* (2013.01); *A61M 2205/3317* (2013.01); *A61M 2205/3331* (2013.01); *A61M 2205/3379* (2013.01); *A61M 2205/3382* (2013.01); *A61M 2205/70* (2013.01); *Y10T 137/6055* (2015.04); *Y10T 137/789* (2015.04)

(58) Field of Classification Search
CPC ...... A61F 2/00; A61F 2/02; A61F 2/04; F16K 15/14; F16K 5/02; F16K 51/00
See application file for complete search history.

(56) References Cited

U.S. PATENT DOCUMENTS

| | | |
|---|---|---|
| 3,367,332 A | 2/1968 | Groves |
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,321,020 A | 3/1982 | Mital |
| 4,331,147 A | 5/1982 | Armstrong |
| 4,382,441 A | 5/1983 | Svedman |
| 4,524,064 A | 6/1985 | Nambu |
| 4,569,674 A | 2/1986 | Phillips et al. |
| 4,578,060 A | 3/1986 | Huck et al. |
| 4,585,397 A | 4/1986 | Crawford et al. |
| 4,604,313 A | 8/1986 | McFarland et al. |
| 4,655,754 A | 4/1987 | Richmond et al. |
| 4,743,232 A | 5/1988 | Kruger |
| 4,758,238 A | 7/1988 | Sundblom et al. |
| 4,767,417 A | 8/1988 | Boehringer et al. |
| 4,826,494 A | 5/1989 | Richmond et al. |
| 4,832,299 A | 5/1989 | Gorton Lanny et al. |
| 4,840,770 A | 6/1989 | Walz et al. |
| 4,865,816 A | 9/1989 | Walz et al. |
| 4,870,975 A | 10/1989 | Cronk et al. |
| 4,969,880 A | 11/1990 | Zamierowski |
| 4,979,944 A | 12/1990 | Luzsicza |
| 4,988,344 A | 1/1991 | Reising et al. |
| 4,988,345 A | 1/1991 | Reising |
| 4,990,137 A | 2/1991 | Graham |
| 4,997,438 A | 3/1991 | Nipper |
| 5,071,104 A | 12/1991 | Witt et al. |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,135,485 A | 8/1992 | Cohen et al. |
| 5,141,503 A | 8/1992 | Sewell, Jr. |
| 5,141,504 A | 8/1992 | Herweck et al. |
| 5,149,331 A | 9/1992 | Ferdman et al. |
| 5,152,757 A | 10/1992 | Eriksson |
| 5,156,602 A | 10/1992 | Steffler |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,219,428 A | 6/1993 | Stern |
| 5,246,353 A | 9/1993 | Sohn |
| 5,261,893 A | 11/1993 | Zamierowski |
| 5,263,922 A | 11/1993 | Sova et al. |
| D352,463 S | 11/1994 | Kubo |
| 5,360,445 A | 11/1994 | Goldowsky |
| 5,386,735 A | 2/1995 | Langdon |
| 5,397,299 A | 3/1995 | Karwoski et al. |
| 5,411,474 A | 5/1995 | Ott et al. |
| 5,458,586 A | 10/1995 | Adiletta |
| D364,679 S | 11/1995 | Heaton et al. |
| 5,466,229 A | 11/1995 | Elson |
| 5,484,427 A | 1/1996 | Gibbons |
| 5,484,428 A | 1/1996 | Drainville et al. |
| 5,527,293 A | 6/1996 | Zamierowski |
| 5,536,233 A | 7/1996 | Khouri |
| 5,549,584 A | 8/1996 | Gross |
| 5,582,601 A | 12/1996 | Wortrich et al. |
| 5,584,824 A | 12/1996 | Gillette et al. |
| 5,588,958 A | 12/1996 | Cunningham et al. |
| 5,591,297 A | 1/1997 | Ahr |
| 5,630,855 A | 5/1997 | Lundbaeck |
| 5,636,643 A | 6/1997 | Argenta et al. |
| 5,645,081 A | 7/1997 | Argenta et al. |
| 5,656,027 A | 8/1997 | Ellingboe |
| 5,669,892 A | 9/1997 | Keogh et al. |
| 5,678,564 A | 10/1997 | Lawrence et al. |
| 5,685,214 A | 11/1997 | Neff et al. |
| 5,693,013 A | 12/1997 | Geuder |
| 5,701,917 A | 12/1997 | Khouri |
| 5,707,173 A | 1/1998 | Cottone et al. |
| 5,733,305 A | 3/1998 | Fleischmann |
| 5,785,700 A | 7/1998 | Olson |
| 5,787,928 A | 8/1998 | Allen et al. |
| 5,807,359 A | 9/1998 | Bemis et al. |
| D400,249 S | 10/1998 | Holubar et al. |
| 5,840,049 A | 11/1998 | Tumey et al. |
| 5,876,387 A | 3/1999 | Killian et al. |
| 5,882,743 A | 3/1999 | McConnell |
| D408,625 S | 4/1999 | Barker |
| 5,911,222 A | 6/1999 | Lawrence et al. |
| 5,944,703 A | 8/1999 | Dixon et al. |
| 5,960,837 A | 10/1999 | Cude |
| 6,010,524 A | 1/2000 | Fleischmann |
| 6,010,527 A | 1/2000 | Augustine et al. |
| 6,071,267 A | 6/2000 | Zamierowski |
| 6,075,177 A | 6/2000 | Bahia et al. |
| 6,099,493 A | 8/2000 | Swisher |
| 6,102,205 A | 8/2000 | Greff et al. |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,168,758 B1 | 1/2001 | Forsberg et al. |
| 6,174,306 B1 | 1/2001 | Fleischmann |
| 6,203,563 B1 | 3/2001 | Fernandez |
| 6,261,276 B1 | 7/2001 | Reitsma |
| D449,891 S | 10/2001 | Norio Moro |
| 6,325,788 B1 | 12/2001 | McKay |
| 6,345,623 B1 | 2/2002 | Heaton et al. |
| 6,348,423 B1 | 2/2002 | Griffiths et al. |

(56) References Cited

U.S. PATENT DOCUMENTS

| | | | |
|---|---|---|---|
| 6,352,233 B1 | 3/2002 | Barberich |
| D456,514 S | 4/2002 | Brown et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,468,199 B1 | 10/2002 | Satou et al. |
| 6,488,643 B1 | 12/2002 | Tumey et al. |
| 6,500,112 B1 | 12/2002 | Khouri |
| 6,501,002 B1 | 12/2002 | Roe et al. |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,132 S | 5/2003 | Randolph |
| D475,134 S | 5/2003 | Randolph |
| 6,557,704 B1 | 5/2003 | Randolph |
| 6,575,333 B1 | 6/2003 | Raboin |
| D477,869 S | 7/2003 | Vijfvinkel |
| D478,659 S | 8/2003 | Hall et al. |
| 6,607,495 B1 | 8/2003 | Skalak et al. |
| 6,620,379 B1 | 9/2003 | Pluk et al. |
| 6,626,891 B2 | 9/2003 | Ohmstede |
| D481,459 S | 10/2003 | Naham |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,723,430 B2 | 4/2004 | Kurata et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,820,483 B1 * | 11/2004 | Beckerman ........... G01F 23/243 73/290 R |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,868,739 B1 | 3/2005 | Krivitski et al. |
| 6,885,116 B2 | 4/2005 | Knirck et al. |
| D504,953 S | 5/2005 | Ryan |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| D516,217 S | 2/2006 | Brown et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| D522,657 S | 6/2006 | Murphy et al. |
| 7,066,949 B2 | 6/2006 | Gammons et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hanningan et al. |
| 7,153,294 B1 | 12/2006 | Farrow |
| 7,169,151 B1 | 1/2007 | Lytinas |
| 7,182,758 B2 | 2/2007 | McCraw |
| D537,944 S | 3/2007 | Eda et al. |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| D580,285 S | 11/2008 | Hendrickson et al. |
| D581,042 S | 11/2008 | Randolph et al. |
| D581,522 S | 11/2008 | Randolph et al. |
| D585,137 S | 1/2009 | Onoda et al. |
| 7,503,910 B2 | 3/2009 | Adahan |
| D590,934 S | 4/2009 | Randolph et al. |
| 7,524,315 B2 | 4/2009 | Blott et al. |
| 7,534,927 B2 | 5/2009 | Lockwood et al. |
| D593,676 S | 6/2009 | Locke et al. |
| D594,114 S | 6/2009 | Locke et al. |
| 7,553,306 B1 | 6/2009 | Hunt et al. |
| 7,569,742 B2 | 8/2009 | Haggstrom et al. |
| D602,582 S | 10/2009 | Pidgeon et al. |
| D602,583 S | 10/2009 | Pidgeon et al. |
| D602,584 S | 10/2009 | Pidgeon et al. |
| 7,604,610 B2 | 10/2009 | Shener et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,700,819 B2 | 4/2010 | Ambrosio et al. |
| 7,722,582 B2 | 5/2010 | Lina et al. |
| 7,723,560 B2 | 5/2010 | Lockwood et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,776,028 B2 | 8/2010 | Miller et al. |
| 7,794,450 B2 | 9/2010 | Blott et al. |
| D625,801 S | 10/2010 | Pidgeon et al. |
| 7,837,673 B2 | 11/2010 | Vogel |
| 7,846,141 B2 | 12/2010 | Weston |
| D630,313 S | 1/2011 | Pidgeon et al. |
| D630,725 S | 1/2011 | Pidgeon et al. |
| 7,862,339 B2 | 1/2011 | Mulligan |
| 7,896,856 B2 | 3/2011 | Petrosenko et al. |
| 7,909,805 B2 | 3/2011 | Weston |
| 7,910,791 B2 | 3/2011 | Coffey |
| 7,927,318 B2 | 4/2011 | Risk, Jr. et al. |
| 7,976,519 B2 | 7/2011 | Bubb et al. |
| 7,976,598 B2 | 7/2011 | Matula et al. |
| 7,998,125 B2 | 8/2011 | Weston |
| 8,007,481 B2 | 8/2011 | Schuessler et al. |
| 8,021,348 B2 | 9/2011 | Risk, Jr. et al. |
| 8,034,037 B2 | 10/2011 | Adams et al. |
| 8,048,046 B2 | 11/2011 | Hudspeth et al. |
| 8,061,360 B2 | 11/2011 | Locke et al. |
| 8,062,272 B2 | 11/2011 | Weston |
| 8,100,873 B2 | 1/2012 | Jaeb et al. |
| 8,167,869 B2 | 5/2012 | Wudyka |
| 8,168,848 B2 | 5/2012 | Lockwood et al. |
| 8,172,817 B2 | 5/2012 | Michaels et al. |
| 8,177,763 B2 | 5/2012 | Wiesner |
| 8,216,198 B2 | 7/2012 | Heagle et al. |
| 8,235,972 B2 | 8/2012 | Adahan |

(56) References Cited

U.S. PATENT DOCUMENTS

| | | |
|---|---|---|
| 8,240,470 B2 | 8/2012 | Pidgeon et al. |
| 8,246,607 B2 | 8/2012 | Karpowicz et al. |
| 8,251,979 B2 | 8/2012 | Malhi |
| 8,257,327 B2 | 9/2012 | Blott et al. |
| 8,257,328 B2 | 9/2012 | Augustine et al. |
| 8,267,909 B2 | 9/2012 | Clementi et al. |
| 8,267,918 B2 | 9/2012 | Johnson et al. |
| 8,294,586 B2 | 10/2012 | Pidgeon et al. |
| 8,308,714 B2 | 11/2012 | Weston et al. |
| 8,323,264 B2 | 12/2012 | Weston et al. |
| 8,333,744 B2 | 12/2012 | Hartwell et al. |
| 8,348,910 B2 | 1/2013 | Blott et al. |
| 8,372,049 B2 | 2/2013 | Jaeb et al. |
| 8,414,519 B2 | 4/2013 | Hudspeth et al. |
| 8,444,392 B2 | 5/2013 | Turner et al. |
| 8,494,349 B2 | 7/2013 | Gordon |
| 8,551,060 B2 | 10/2013 | Schuessler et al. |
| 8,551,061 B2 | 10/2013 | Hartwell et al. |
| 8,568,386 B2 | 10/2013 | Malhi |
| 8,617,129 B2 | 12/2013 | Hartwell |
| 8,622,981 B2 | 1/2014 | Hartwell et al. |
| 8,641,691 B2 | 2/2014 | Fink et al. |
| 8,652,111 B2 | 2/2014 | Pratt et al. |
| 8,679,081 B2 | 3/2014 | Heagle et al. |
| 8,747,376 B2 | 6/2014 | Locke et al. |
| 8,771,259 B2 | 7/2014 | Karpowicz et al. |
| 8,814,840 B2 | 8/2014 | Evans et al. |
| 8,814,841 B2 | 8/2014 | Hartwell |
| 8,827,983 B2 | 9/2014 | Braga et al. |
| 8,834,452 B2 | 9/2014 | Hudspeth et al. |
| 8,843,327 B2 | 9/2014 | Vernon-Harcourt et al. |
| 8,845,603 B2 | 9/2014 | Middleton et al. |
| 8,974,429 B2 | 3/2015 | Gordon et al. |
| 9,019,681 B2 | 4/2015 | Locke et al. |
| 9,050,399 B2 | 6/2015 | Hartwell |
| 9,205,183 B2 | 12/2015 | Hartwell et al. |
| 9,205,235 B2 | 12/2015 | Wiesner |
| 9,211,486 B2 | 12/2015 | Locke et al. |
| 9,227,000 B2 | 1/2016 | Fink et al. |
| 9,272,078 B2 | 3/2016 | Jaeb et al. |
| 9,320,838 B2 | 4/2016 | Hartwell et al. |
| 9,375,521 B2 | 6/2016 | Hudspeth et al. |
| 9,408,954 B2 | 8/2016 | Gordon et al. |
| 9,415,145 B2 | 8/2016 | Braga et al. |
| 9,561,312 B2 | 2/2017 | Heaton et al. |
| 9,636,440 B2 | 5/2017 | Weston et al. |
| 9,642,955 B2 | 5/2017 | Fink et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0026160 A1 | 2/2002 | Takahashi et al. |
| 2002/0143286 A1 | 10/2002 | Tumey |
| 2002/0145012 A1 | 10/2002 | Ho |
| 2002/0151836 A1 | 10/2002 | Burden |
| 2002/0156464 A1 | 10/2002 | Blischak et al. |
| 2003/0093041 A1 | 5/2003 | Risk, Jr. et al. |
| 2003/0101826 A1 | 6/2003 | Neubert |
| 2003/0163101 A1 | 8/2003 | Say |
| 2003/0164600 A1 | 9/2003 | Dunn et al. |
| 2003/0181850 A1 | 9/2003 | Diamond et al. |
| 2003/0212357 A1 | 11/2003 | Pace |
| 2003/0212359 A1 | 11/2003 | Butler |
| 2003/0219469 A1 | 11/2003 | Johnson et al. |
| 2003/0235635 A1 | 12/2003 | Fong et al. |
| 2004/0006321 A1 | 1/2004 | Cheng et al. |
| 2004/0039415 A1 | 2/2004 | Zamierowski |
| 2004/0054338 A1 | 3/2004 | Byvordi |
| 2004/0064132 A1 | 4/2004 | Boehringer et al. |
| 2004/0087918 A1 | 5/2004 | Johnson, III et al. |
| 2004/0093026 A1 | 5/2004 | Weidenhagen et al. |
| 2004/0102743 A1 | 5/2004 | Walker |
| 2004/0122434 A1 | 6/2004 | Argenta et al. |
| 2004/0153029 A1 | 8/2004 | Blischak et al. |
| 2004/0167482 A1 | 8/2004 | Watson |
| 2004/0180093 A1 | 9/2004 | Burton et al. |
| 2004/0193218 A1 | 9/2004 | Butler |
| 2004/0233631 A1 | 11/2004 | Lord |
| 2004/0241213 A1 | 12/2004 | Bray |
| 2005/0020955 A1 | 1/2005 | Sanders et al. |
| 2005/0085795 A1 | 4/2005 | Lockwood et al. |
| 2005/0090787 A1 | 4/2005 | Risk, Jr. et al. |
| 2005/0124966 A1 | 6/2005 | Karpowicz et al. |
| 2005/0144711 A1 | 7/2005 | Valadez et al. |
| 2005/0166683 A1 | 8/2005 | Krivitski et al. |
| 2005/0177190 A1 | 8/2005 | Zamierowski |
| 2005/0182445 A1 | 8/2005 | Zamierowski |
| 2005/0187528 A1 | 8/2005 | Berg |
| 2005/0209560 A1 | 9/2005 | Boukhny et al. |
| 2005/0248045 A1 | 11/2005 | Anthony |
| 2006/0029675 A1 | 2/2006 | Ginther |
| 2006/0039742 A1 | 2/2006 | Cable, Jr. et al. |
| 2006/0059980 A1 | 3/2006 | Matsubara et al. |
| 2006/0100586 A1 | 5/2006 | Karpowicz et al. |
| 2006/0129137 A1 | 6/2006 | Lockwood et al. |
| 2006/0144440 A1 | 7/2006 | Merkle |
| 2006/0149170 A1 | 7/2006 | Boynton et al. |
| 2006/0149171 A1 | 7/2006 | Vogel et al. |
| 2006/0229575 A1 | 10/2006 | Boiarski |
| 2006/0280650 A1 | 12/2006 | Wong et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0032741 A1 | 2/2007 | Hibner et al. |
| 2007/0032754 A1 | 2/2007 | Walsh |
| 2007/0032755 A1 | 2/2007 | Walsh |
| 2007/0032763 A1 | 2/2007 | Vogel |
| 2007/0032778 A1 | 2/2007 | Heaton et al. |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0135779 A1 | 6/2007 | Lalomia et al. |
| 2007/0179460 A1 | 8/2007 | Adahan |
| 2007/0180904 A1 | 8/2007 | Gao |
| 2007/0219513 A1 | 9/2007 | Lina et al. |
| 2007/0219532 A1 | 9/2007 | Karpowicz et al. |
| 2007/0219535 A1 | 9/2007 | Phung et al. |
| 2007/0233022 A1 | 10/2007 | Henley et al. |
| 2007/0260226 A1 | 11/2007 | Jaeb et al. |
| 2008/0011667 A1 | 1/2008 | Ruschke |
| 2008/0015526 A1 | 1/2008 | Reiner et al. |
| 2008/0033400 A1 | 2/2008 | Holper et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0082077 A1 | 4/2008 | Williams |
| 2008/0125697 A1 | 5/2008 | Gao |
| 2008/0125698 A1 | 5/2008 | Gerg et al. |
| 2008/0156092 A1 | 7/2008 | Boiarski |
| 2008/0183233 A1 | 7/2008 | Koch et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0243096 A1 | 10/2008 | Svedman |
| 2008/0281281 A1 | 11/2008 | Meyer et al. |
| 2009/0005746 A1 | 1/2009 | Nielsen et al. |
| 2009/0012484 A1 | 1/2009 | Nielsen et al. |
| 2009/0036873 A1 | 2/2009 | Nielsen et al. |
| 2009/0043268 A1 | 2/2009 | Eddy et al. |
| 2009/0099519 A1 | 4/2009 | Kaplan |
| 2009/0101219 A1 | 4/2009 | Martini et al. |
| 2009/0157016 A1 | 6/2009 | Adahan |
| 2009/0204049 A1 | 8/2009 | Lee |
| 2009/0240218 A1 | 9/2009 | Braga et al. |
| 2009/0254066 A1 | 10/2009 | Heaton |
| 2009/0299251 A1 | 12/2009 | Buan |
| 2009/0299306 A1 | 12/2009 | Buan |
| 2009/0312725 A1 | 12/2009 | Braga |
| 2010/0022990 A1 | 1/2010 | Karpowicz et al. |
| 2010/0030132 A1 | 2/2010 | Niezgoda et al. |
| 2010/0036333 A1 | 2/2010 | Schenk, III et al. |

(56) References Cited

U.S. PATENT DOCUMENTS

| | | |
|---|---|---|
| 2010/0042059 A1 | 2/2010 | Pratt et al. |
| 2010/0121257 A1 | 5/2010 | King |
| 2010/0126268 A1 | 5/2010 | Baily et al. |
| 2010/0145289 A1 | 6/2010 | Line et al. |
| 2010/0191178 A1 | 7/2010 | Ross et al. |
| 2010/0211030 A1 | 8/2010 | Turner et al. |
| 2010/0268179 A1 | 10/2010 | Kelch et al. |
| 2010/0280435 A1 | 11/2010 | Raney et al. |
| 2010/0280536 A1 | 11/2010 | Hartwell |
| 2010/0305490 A1 | 12/2010 | Coulthard et al. |
| 2011/0038741 A1 | 2/2011 | Lissner et al. |
| 2011/0054810 A1 | 3/2011 | Turner |
| 2011/0063117 A1 | 3/2011 | Turner |
| 2011/0066110 A1 | 3/2011 | Fathallah et al. |
| 2011/0071415 A1 | 3/2011 | Karwoski et al. |
| 2011/0077605 A1 | 3/2011 | Karpowicz et al. |
| 2011/0092958 A1 | 4/2011 | Jacobs |
| 2011/0112493 A1 | 5/2011 | Koch et al. |
| 2011/0130712 A1 | 6/2011 | Topaz |
| 2011/0251569 A1 | 10/2011 | Turner et al. |
| 2011/0313375 A1 | 12/2011 | Michaels |
| 2012/0001762 A1 | 1/2012 | Turner et al. |
| 2012/0035560 A1 | 2/2012 | Eddy et al. |
| 2012/0046625 A1 | 2/2012 | Johannison |
| 2013/0090613 A1 | 4/2013 | Kelch et al. |
| 2013/0144235 A1 | 6/2013 | Augustine et al. |
| 2014/0128822 A1 | 5/2014 | Malhi |
| 2014/0163491 A1 | 6/2014 | Schuessler |
| 2014/0207091 A1 | 7/2014 | Heagle |
| 2014/0236106 A1 | 8/2014 | Locke et al. |
| 2014/0320283 A1 | 10/2014 | Lawhorn |
| 2015/0073363 A1 | 3/2015 | Kelch et al. |
| 2015/0343122 A1 | 12/2015 | Hartwell |
| 2016/0144081 A1 | 5/2016 | Wiesner |
| 2016/0151547 A1 | 6/2016 | Hartwell et al. |
| 2016/0184498 A1 | 6/2016 | Jaeb et al. |
| 2016/0325025 A1 | 11/2016 | Hudspeth et al. |
| 2016/0331877 A1 | 11/2016 | Braga et al. |
| 2017/0281424 A1 | 10/2017 | Fink et al. |
| 2018/0333521 A1 | 11/2018 | Hudspeth et al. |
| 2018/0353352 A1 | 12/2018 | Fink et al. |
| 2019/0001030 A1 | 1/2019 | Braga et al. |
| 2019/0009008 A1 | 1/2019 | Hartwell |
| 2019/0060532 A1 | 2/2019 | Hartwell et al. |
| 2019/0099527 A1 | 4/2019 | Schuessler et al. |

FOREIGN PATENT DOCUMENTS

| | | |
|---|---|---|
| DE | 10 60 097 | 6/1959 |
| DE | 41 11 122 A1 | 4/1993 |
| DE | 43 12 852 | 10/1993 |
| DE | 295 04 378 U1 | 10/1995 |
| EP | 0 020 662 | 7/1984 |
| EP | 0 358 302 | 3/1990 |
| EP | 0 853 950 | 7/1998 |
| EP | 2 248 546 | 11/2010 |
| EP | 2 066 365 | 4/2015 |
| GB | 1 415 096 | 11/1975 |
| GB | 1 549 756 | 8/1979 |
| GB | 2 195 255 A | 4/1988 |
| GB | 2 235 877 | 3/1991 |
| GB | 2 235 877 A | 3/1991 |
| GB | 2418738 | 4/2006 |
| JP | 11-300142 | 11/1999 |
| JP | 2000-202022 | 7/2000 |
| JP | 2006-043523 | 2/2006 |
| JP | 2007-024421 | 2/2007 |
| SU | 1762940 | 1/1989 |
| WO | WO 1980/01139 | 6/1980 |
| WO | WO 1980/02182 | 10/1980 |
| WO | WO 1984/01904 | 5/1984 |
| WO | WO 1987/00439 | 1/1987 |
| WO | WO 1989/05133 | 6/1989 |
| WO | WO 1992/19313 | 11/1992 |
| WO | WO 1996/05873 | 2/1996 |
| WO | WO 1996/19335 | 6/1996 |
| WO | WO 1997/14450 | 4/1997 |
| WO | WO 2003/022333 | 3/2003 |
| WO | WO 2003/053346 | 7/2003 |
| WO | WO 2003/057307 | 7/2003 |
| WO | WO 2003/074106 | 9/2003 |
| WO | WO 2003/101508 | 12/2003 |
| WO | WO 2005/009488 | 2/2005 |
| WO | WO 2005/105179 | 11/2005 |
| WO | WO 2006/052745 | 5/2006 |
| WO | WO 2007/031757 | 3/2007 |
| WO | WO 2008/013896 | 1/2008 |
| WO | WO 2008/036344 | 3/2008 |
| WO | WO 2008/036360 | 3/2008 |
| WO | WO 2008/039314 | 4/2008 |
| WO | WO 2008/040020 | 4/2008 |
| WO | WO 2008/048481 | 4/2008 |
| WO | WO 2008/049029 | 4/2008 |
| WO | WO 2008/13896 | 11/2008 |
| WO | WO 2009/004289 | 1/2009 |
| WO | WO 2009/007702 | 1/2009 |
| WO | WO 2009/077722 | 6/2009 |
| WO | WO 2009/086580 | 7/2009 |
| WO | WO 2009/151645 | 12/2009 |
| WO | WO 2010/017484 | 2/2010 |
| WO | WO 2010/021783 | 2/2010 |
| WO | WO 2010/039481 | 4/2010 |
| WO | WO 2010/089368 | 8/2010 |

OTHER PUBLICATIONS

US 7,186,244 B1, 03/2007, Hunt et al. (withdrawn)
The American Heritage® Science Dictionary Copyright © 2005, in 3 pages.
Huntleigh Healthcare, "Negative Pressure Positive Outcomes" WoundASSIST TNP Console and Canister Brochure, 2007, in 6 pages.
Fleischmann, W. et al., "Vacuum Sealing: Indication, Technique and Results", Emr J Orthop Surg Tramatol (1995) 5:37-40.
Aubrey, D.A. et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bier, A., Hyperemia as a Therapeutic Agent, Ed. Dr. Gustavus M. Blech, A. Robertson & Co., Chicago 1905.
Arnljots, et al., "Irrigation Treatment in Split-thickness Skin Grafting of Intractable Leg Ulcers," Scand J Plast Reconstr Surg 19: 211-213,1985.
Bucalo et al. "Inhibition of Cell Proliferation by Chronic Wound Fluid." Wound Repair and Regeneration. Miami, 1993. pp. 181-186.
Chardack et al., "Experimental Studies on Synthetic Substitutes for Skin and Their Use in the Treatment of Burns," vol. 155, No. 1 (128-136), 1961.
Chariker, M.E., et al, "Effective Management of Incisional and Cutaneous Fistulae with Closed Suction Wound Drainage," Contemporary Surgery. Jun. 1989, pp. 59-63, vol. 34.
Edlich, R.F., et al.: "Evaluation of a New, Improved Surgical Drainage System," The American Journal of Surgery, vol. 149, pp. 295-298, Feb. 1985.
Fleischmann, "Vacuum Sealing for Treatment of Problematical Wounds", University Surgical Clinic and Polyclinic—Accident Surgery Department, WundForum Spezial-IHW, 1994.
Garcia-Rinaldi, R., et al., Improving the Efficiency of Wound Drainage Catheters, Amer. Journ. of Surg., Sep. 1975, 130, 372-373.
Gorica Zivadinovic, et al., "Vacuum Therapy in the Treatment of Peripheral Blood Vessels," Conference Papers of the 5th Timok Medical Days, Majdanpek, 1986 (161-164).
Health Technology, Literature R., "Vacuum Assisted Closure Therapy for Wound Care", Health Technology Literature Review (Dec. 2004), 3-59.

(56) References Cited

OTHER PUBLICATIONS

Jeter, Katherine F., et al., "Managing Draining Wounds and Fistulae: New and Established Methods", Chronic Wound Care, 1990, pp. 240-246.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Kostiuchenok, et al., "The Vacuum Effect in the Surgical Treatment of Purulent Wounds," Russian Journal: Vestnik Khirurgii, Sep. 1986, (18-21).
McLaughlan, James, Sterile Microenvironment for Postoperative Wound Care, The Lancet, pp. 503-504, Sep. 2, 1978.
Meyer, MD., et al., "In Surgery, Medicine and the Specialties a Manual of its Practical Application", Bier's Hyperemic Treatment, Second Revised Edition, W.B. Saunders Company, 1909.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Mulder, GD, et al., "Clinicians' Pocket Guide to Chronic Wound Repair," Wound Healing Publications Second Edition, 1991.
RENASYS EZ System for Negative Wound Therapy, Smith & Nephew announcement, dated Feb. 24, 2009, in 3 pages.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (322-326).
Sames, C.P., Sealing of Wounds with Vacuum Drainage, Br. Med. Journ., Nov. 5, 1977, p. 1223, Correspondence.
Sandén, Göran MD., et al., "Staphylococcal Wound Infection in the Pig: Part II. Inoculation, Quantification of Bacteria, and Reproducibility," Annals of Plastic Surgery, vol. 23, No. 3, Sep. 1989, (219-223).
Stewart, Joanne, Ph.D., World Wide Wounds—Next generation of products for wound management—2002 (13 pages).
Stoll, "Energetic Remedies—Cupping: Healing Within a Vacuum," https://www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, P., "Irrigation Treatment of Leg Ulcers," The Lancet, Sep. 3, 1983 (532-534).
Svedman, et al., "Staphylococcal Wound Infection in the Pig: Part I. Course," Annals of Plastic Surgery, vol. 23, No. 3, Sep. 1989 (212-218).
Teder et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-13, 1972 vol. 105.
Usupov, et al., "Active Wound Drainage," Russian Journal: Vestnik Khirugii, Apr. 1987, (42-45).
Wu, W.S., et al. Vacuum therapy as an intermediate phase in wound closure: a clinical experience, Eur J Past Surg (2000) 23: 174-177.
Davydov, Y. et al., "Bacteriological and Cytological Assessment of Vacuum Therapy of Purulent Wounds", Vestnik Khirurgii, Oct. 1988, (48-52).
Davydov, Y. et al., "Concepts for Clinical Biological Management of the Wound Process in the Treatment of Purulent Wounds Using Vacuum Therapy," Vestnik Khirurgii, Feb. 1991, 132-135).
Davydov, Y. et al., "Vacuum Therapy in the Treatment of Purulent Lactation Mastitis," Russian Journal: Vesnik Khirurgii, Sep. 1986, (66-70).
Davydov, Y. et al., "Vacuum Therapy in treatment of Acute Purulent Diseases of Soft Tissues and Purulent Wounds," Vestnik Khirurgii, (Surgeon's Herald), Medicine Publishers, 1986.
Piaggesi, A. et al., "SNAP® Wound Care System Made Easy", Wounds International, vol. 3(1), Feb. 2012, in 6 pages. URL: http://www.woundsinternational.com.
International Search Report, re PCT Application No. PCT/US2009/047463, dated Aug. 7, 2009.
International Preliminary Report on Patentability, re PCT Application No. PCT/US2009/047463, dated Mar. 3, 2011.
KCI, "V.A.C. Freedom User's Guide", May 2002, in 16 pages.

\* cited by examiner

SENSOR WITH ELECTRICAL CONTACT PROTECTION FOR USE IN FLUID COLLECTION CANISTER AND NEGATIVE PRESSURE WOUND THERAPY SYSTEMS INCLUDING SAME

CROSS-REFERENCE TO RELATED PATENT APPLICATIONS

This patent application is a continuation of U.S. patent application Ser. No. 15/219,045 filed on Jul. 25, 2016, which is a continuation of U.S. patent application Ser. No. 14/473,063 filed on Aug. 29, 2014, which is a continuation of U.S. patent application Ser. No. 12/471,789 filed on May 26, 2009, which claims priority to U.S. Provisional Patent Application No. 61/090,782 filed on Aug. 21, 2008, entitled "WOUND THERAPY SYSTEM WITH CANISTER FILL DETECTOR", the disclosures of which are herein incorporated by reference in their entirety.

BACKGROUND

Technical Field

The present disclosure relates to negative pressure wound therapy systems and, more particularly, to a sensor with electrical contact protection for use in a fluid collection canister and negative pressure wound therapy systems including the same.

Description of Related Art

Negative pressure therapy, also known as suction or vacuum therapy, has been used in treating and healing wounds. Treating an open wound by applying negative pressure, e.g., reduced or sub-atmospheric pressure, to a localized reservoir over a wound has been found to assist in closing the wound by increasing blood circulation at the wound area, stimulating the formation of granulation tissue and promoting the migration of healthy tissue over the wound. Negative pressure therapy may also inhibit bacterial growth by drawing wound fluids from the wound such as exudate, which may tend to harbor bacteria. Negative pressure therapy can thus be applied as a healing modality for its antiseptic and tissue regeneration effects. This technique has proven effective for treating a variety of wound conditions, including chronic or healing-resistant wounds and ulcers, and is also used for other purposes such as post-operative wound care.

Generally, negative pressure therapy provides for a wound covering to be positioned over the wound to facilitate suction at the wound area. A conduit is introduced through the wound covering to provide fluid communication to an external vacuum source, such as a hospital vacuum system or a portable vacuum pump. Atmospheric gas, wound exudate or other fluids may thus be drawn from the reservoir through the fluid conduit to stimulate healing of the wound. Generally, a fluid collection canister for collecting fluids aspirated from the wound is positioned in the suction line between the wound covering and the vacuum source. Exudate drawn from the reservoir through the fluid conduit may thus be deposited into the collection canister, which may be disposable.

The fluid collection canister of the wound therapy system may need to be disconnected or replaced for a variety of reasons, such as when filled with exudate. A mechanism for preventing overfilling of the collection canister may prevent fluid contamination of various components of the negative pressure wound therapy system and help to prevent spillage or leakage. During a treatment, the collection canister may be prevented from overfilling by a hydrophobic filter at the top of the collection canister that shuts off the air flow to the vacuum source when the collection canister is full. During some treatments, the collection canister is replaced or emptied of exudate on a regular scheduled basis, e.g., every few days or so. The collection canister may fill more quickly than anticipated. If this occurs, therapy cannot be delivered to the wound until the collection canister is emptied or replaced. There is a need for a negative pressure wound therapy system that is capable of providing an indication to alert the user that the collection canister must be emptied or replaced.

SUMMARY

The present disclosure relates to a sensor for use in a canister for fluid collection, the canister having a canister top and defining a fluid collection chamber. The sensor includes a first electrode and a second electrode. The first electrode includes a first portion and a second portion, wherein the first portion of the first electrode is supported by the canister top, and the second portion of the first electrode is configured to extend into the fluid collection chamber. The second electrode includes a first portion and a second portion, wherein the first portion of the second electrode is supported by the canister top, and the second portion of the second electrode is configured to extend into the fluid collection chamber. The sensor also includes an electric circuit configured to detect an electrical property associated with the first and second electrodes. The second portions of the first and second electrodes may be at least partly covered with a coating to inhibit encrustation formed by drying of exudate. The sensor may also include an inner chamber disposed within the fluid collection chamber, the inner chamber bounded by the canister top, an inner wall and a bottom end, wherein the second portions of the first and second electrodes are disposed within the inner chamber. At least a portion of the bottom end of the inner chamber may be formed of a water-soluble film.

The present disclosure also relates to a portable negative pressure wound therapy apparatus including a dressing assembly for positioning over a wound to apply a negative pressure to the wound and a canister assembly in fluid communication with the dressing assembly. The canister assembly includes a control unit, a vacuum source disposed in the control unit, a pressure sensor in communication with the control unit, and a collection canister. The collection canister includes an inlet conduit in fluid communication with the dressing assembly, a chamber to collect wound fluids from the dressing assembly, an inlet port coupled to the inlet conduit to introduce the wound fluids from the dressing assembly into the chamber, and a suction port to communicate with the chamber and the vacuum source. The canister assembly may also include a transducer port to communicate with the chamber and the pressure sensor.

The present disclosure also relates to a system for negative pressure therapy in connection with healing a wound including a dressing assembly for positioning relative to a wound bed and a negative pressure mechanism. The negative pressure mechanism includes a control unit, a collection canister for collecting exudate removed from the wound bed under negative pressure supplied by the control unit, and a detector circuit. The detector circuit includes first and second electrically conductive contacts disposed within the collection canister and an indicator adapted to provide a perceptible indication when exudate makes contact with the first and second electrically conductive contacts. The detector circuit is open in the absence of exudate making contact with the first and second electrically conductive contacts. The detector circuit is closed when exudate makes contact with the first and second electrically conductive contacts. The first and second electrically conductive contacts may be mounted at a position within the collection canister corresponding to a maximum fill volume of the collection canister.

BRIEF DESCRIPTION OF THE DRAWINGS

Objects and features of the presently disclosed negative pressure wound therapy systems and sensors for use therein will become apparent to those of ordinary skill in the art when descriptions of various embodiments thereof are read with reference to the accompanying drawings, of which.

DETAILED DESCRIPTION

Figure 1:
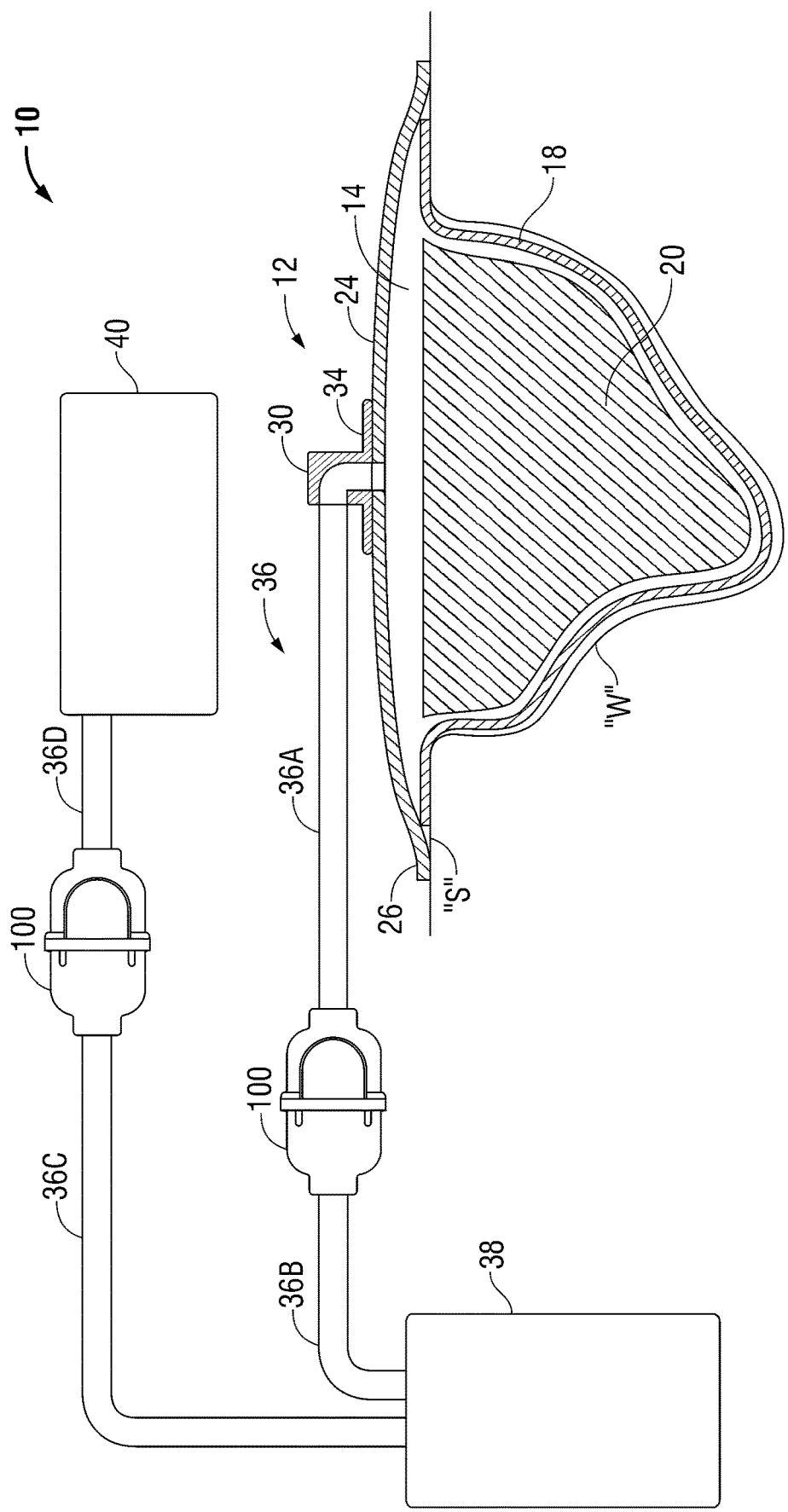
FIG. 1 is a schematic diagram of an embodiment of a negative pressure wound therapy system in accordance with the present disclosure.

Various embodiments of the present disclosure provide negative pressure wound therapy systems (or apparatus) including a collection canister having a chamber to collect wound fluids. Embodiments of the presently disclosed negative pressure wound therapy systems are generally suitable for use in applying negative pressure to a wound to facilitate healing of the wound in accordance with various treatment modalities. Embodiments of the presently disclosed negative pressure wound therapy systems are entirely portable and may be worn or carried by the user such that the user may be completely ambulatory during the therapy period. Embodiments of the presently disclosed negative pressure wound therapy apparatus and components thereof may be entirely reusable or may be entirely disposable after a predetermined period of use or may be individually disposable whereby some of the components are reused for a subsequent therapy application.

Hereinafter, embodiments of the presently disclosed negative pressure wound therapy systems and embodiments of the presently disclosed sensors for use in negative pressure wound therapy systems will be described with reference to the accompanying drawings Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both. As used herein, "transmission line" generally refers to any transmission medium that can be used for the propagation of signals from one point to another.

Referring to FIG. 1, a negative pressure wound therapy apparatus according to an embodiment of the present disclosure is depicted generally as 10 for use on a wound bed "w" surrounded by healthy skin "s". Negative pressure wound therapy apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A non-adherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® nonadherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD™ offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN® II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the negative pressure wound therapy apparatus 10 illustrated in FIG. 1, the conduit 36 includes a first conduit section 36A, a second conduit section 36B, a third conduit section 36C and a fourth conduit section 360. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 360, which extends to the vacuum source 40. The shape, size and/or number of conduit sections of the conduit 36 may be varied from the first, second, third and fourth conduit sections 36A, 36B, 36C and 360 depicted in FIG. 1.

The first, second, third and fourth conduit sections 36A, 36B, 36C and 360 of the conduit 36 may be connected to components of the apparatus 10 by conventional airtight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. For example, super absorbent polymers (SAP), silica gel, sodium polyacrylate, potassium polyacrylamide or related compounds may be provided within collection canister 38. At least a portion of canister 38 may be transparent or semi-transparent, e.g., to permit a visual assessment of the wound exudate to assist in evaluating the color, quality and/or quantity of exudate. A transparent or semi-transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 360 connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg. One example of a peristaltic pump that may be used as the vacuum source 40 is the commercially available Kangaroo PET Eternal Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the negative pressure wound therapy apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the negative pressure wound therapy apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
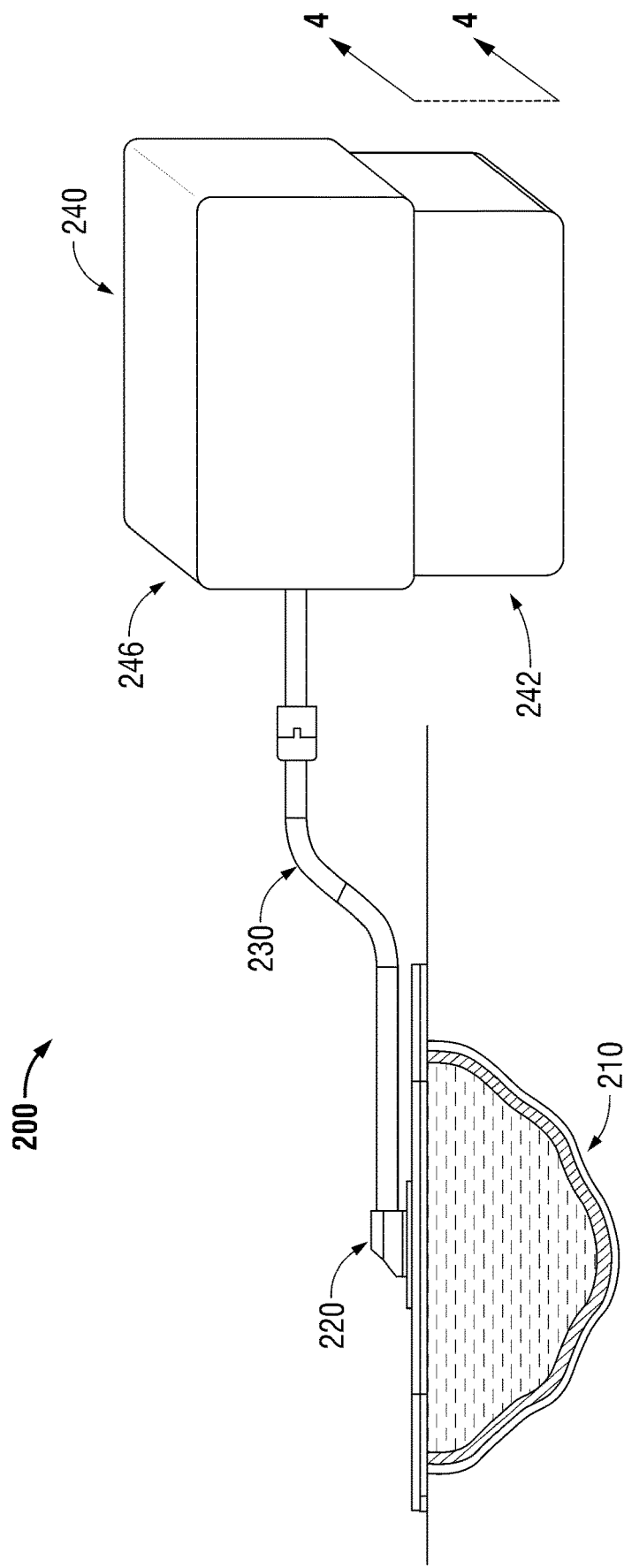
FIG. 2 is a schematic diagram of an embodiment of a negative pressure wound therapy system including a canister assembly in accordance with the present disclosure.

Referring to FIG. 2, the negative pressure wound therapy system shown generally as 200 includes a dressing assembly 210, a wound port assembly 220, an extension assembly 230 and a canister assembly 240. Dressing assembly 210 is positioned relative to the wound area to define a vacuum chamber about the wound area to maintain negative pressure at the wound area. Dressing assembly 210 may be substantially sealed from extraneous air leakage, e.g., using adhesive coverings. Wound port assembly 220 is mounted to the dressing assembly 210. For example, wound port assembly 220 may include a substantially continuous band of adhesive at its periphery for affixing the wound port assembly 220 to the dressing assembly 210. Extension assembly 230 is coupled between the wound port assembly 220 and the canister assembly 240 and defines a fluid flow path between the wound port assembly 220 and the canister assembly 240. A hollow interior of the wound port assembly 220 provides fluid communication between the extension assembly 230 and the interior of the dressing assembly 210. Dressing assembly 210 and the wound port assembly 220 shown in FIG. 2 are similar to components of the wound dressing 12 of FIG. 1 and further description thereof is omitted in the interests of brevity.

Canister assembly 240 includes a control unit 246 and a collection canister 242 disposed below the control unit 246. Control unit 246 and the collection canister 242 may be releasably coupled. Mechanisms for selective coupling and decoupling of the control unit 246 and the collection canister 242 include fasteners, latches, clips, straps, bayonet mounts, magnetic couplings, and other devices. Collection canister 242 may consist of any container suitable for containing wound fluids.

In one embodiment, the negative pressure wound therapy system 200 is capable of operating in a continuous mode or an alternating mode. In the continuous mode, the control unit 246 controls a pump (e.g., suction pump 360 shown in FIG. 3) to continuously supply a selected vacuum level at the collection canister 242 to create a reduced pressure state within the dressing assembly 210. In the alternating mode, the control unit 246 controls the pump to alternating supply a first negative pressure, e.g., about 80 mmHg, at the collection canister 242 for a preset fixed amount of time and a second negative pressure, e.g., about 50 mmHg, at the collection canister 242 for a different preset fixed amount of time.

In general, the output of the pump is directly related to the degree of air leakage in the negative pressure wound therapy system 200 and the open volume in the collection canister 242. If there is sufficient air leakage in the system 200, e.g., at the dressing assembly 210, the pump can remain on continuously and the control unit 246 can control negative pressure at the collection canister 242 by adjusting the pump speed. Alternatively, if there is not sufficient air leakage in the system 200 to permit the pump to remain on continuously, the control unit 246 can control negative pressure at the collection canister 242 by turning the pump on and off, e.g., for non-equal on/off periods of time.

Control unit 246 responds to various sensed events by signaling alarms. Various types of conditions may be signaled by alarms. In embodiments, control unit 246 is capable of signaling alarms for failed pressure sensor condition, use odometer expired condition, watchdog reset condition, failed pump condition, leak condition, replace canister condition, excessive vacuum condition, failed LEDs condition, low battery condition, very low battery condition, and failed battery condition. Priority levels may be associated with alarms. In embodiments, the priority levels of alarms are low priority alarm, medium priority alarm, and system alarm (highest priority). Low priority alarms, when triggered, may be continuously indicated. Medium priority alarms and system alarms, when triggered, may have a flashing indication.

Control unit 246 may stop operation of the pump (e.g., suction pump 360 shown in FIG. 3) in response to an alarm, e.g., depending on alarm type and/or priority level. In embodiments, the control unit 246 stops operation of the pump in response to system alarms, e.g., failed pressure sensor system alarm, use odometer expired system alarm, watchdog reset system alarm, failed pump system alarm, excessive vacuum system alarm, and/or failed LEDs system alarm.

If an air leak develops in the negative pressure wound therapy system 200, e.g., at the dressing assembly 210, for which the control unit 246 cannot compensate by increasing the pump speed, the control unit 246 may indicate an alarm. For example, the control unit 246 may indicate a leak alarm after two consecutive minutes of operation in which the vacuum level is below the current set point (or below the minimum level of a set point range).

Audible indicatory means may also be incorporated or associated with the control unit 246 to notify the user of a condition, e.g., leak, canister assembly tip, failed pressure sensor, failed pump, excessive vacuum, or low battery conditions. The audio indication for some alarm types can be paused by pressing a pause alarm button (not shown).

In embodiments, the control unit 246 includes a user interface (not shown). Control unit 246 also includes a processor (e.g., 310 shown in FIG. 3). A pressure transducer (e.g., transducer 340 shown in FIG. 3) is electrically coupled to the processor. The user turns ON the canister assembly 240 by pressing a power button (not shown). When the power button is pressed, the control unit 246 performs a series of internal checks during power up. In one embodiment, after successfully completing the power-up tasks, the control unit 246 turns on the pump 360 using the stored settings. At initial activation of the canister assembly 240, the stored settings are the default settings. In one embodiment, the default settings for controlling the pump 360 are 80 mmHg and continuous mode. In one embodiment, the currently stored vacuum level setting can be altered by the user, e.g., to 50 mmHg. In one embodiment, the currently stored mode setting can be altered by the user, e.g., to an alternating mode.

Canister assembly 240 may be constructed from a variety of materials such as Lucite™ polycarbonate, metals, metal alloys, plastics, or other durable materials capable of withstanding forces applied during normal use, and may have some capability of withstanding possibly excessive forces resulting from misuse. Collection canister 242 may include a window (e.g., 1223 shown in FIG. 12) with fluid level markings or graduations (e.g., 1225 shown in FIG. 12) for promoting visual assessment of the amount of exudate contained within the collection canister 242. A transparent or partially transparent collection canister 242 may thus assist in determining the remaining capacity of the collection canister 242 and/or when the collection canister 242 should be replaced.

Figure 3:
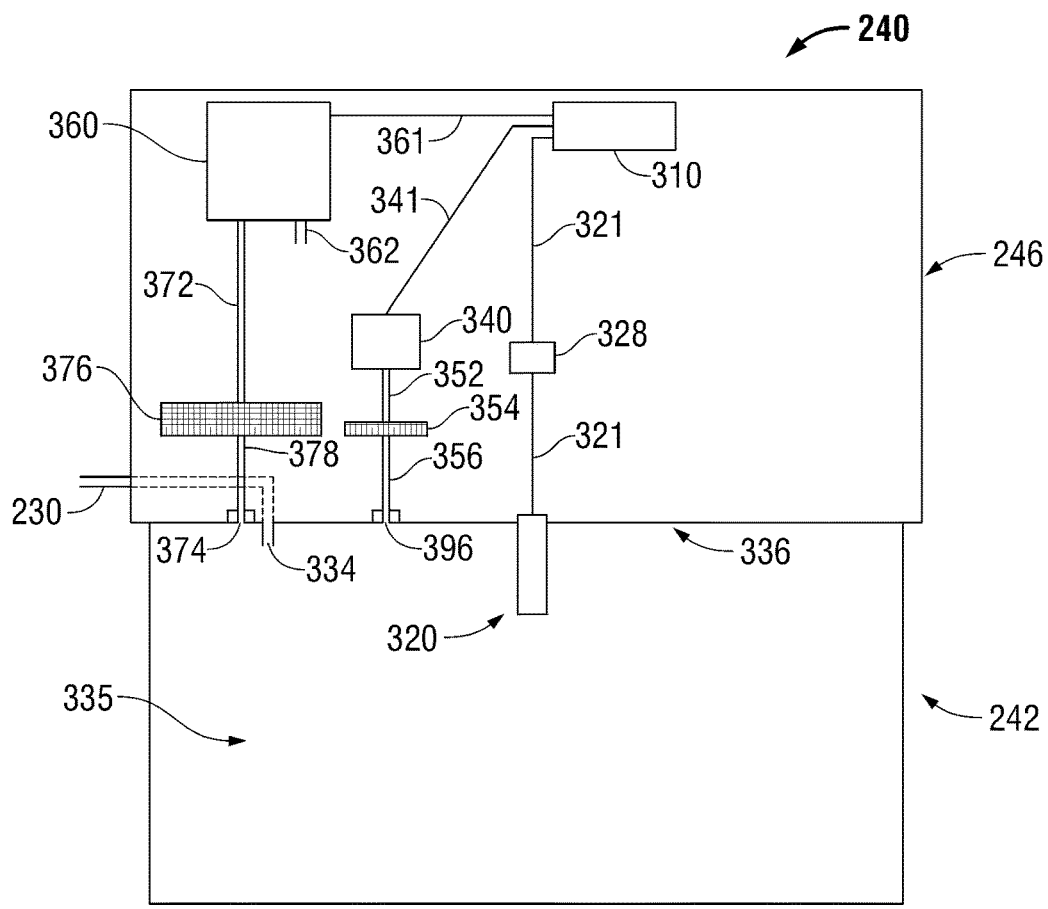
FIG. 3 is a schematic diagram of the canister assembly of the negative pressure wound therapy system illustrated in FIG. 2.

Referring to FIG. 3, an embodiment of the canister assembly 240 illustrated in FIG. 2 is shown and includes a control unit 246 and a collection canister 242. In embodiments, canister assembly 240 is coupled via an extension assembly 230 to a dressing assembly (e.g., wound dressing 12 shown in FIG. 1) to apply negative pressure to a wound to facilitate healing of the wound in accordance with various treatment modalities.

Control unit 246 includes a suction pump 360, a pump inlet conduit 372, a pump outlet conduit 362, a first filter element 376, a transducer 340, a transducer conduit 352, a second filter element 354, a first connecting channel 378 and a second connecting channel 356.

Suction pump 360 may provide negative pressure produced by a piston drawn through a cylinder. Suction pump 360 may be a peristaltic pump or a diaphragm pump. Suction pump 360 may be a manual pump or an automated pump. The automated pump may be in the form of a portable pump, e.g., a small or miniature pump that maintains or draws adequate and therapeutic vacuum levels. In one embodiment, the suction pump 360 is a portable, lightweight, battery-operated, DC motor-driven pump. A vibration damping tape (not shown), e.g., viscoelastic damping tape, may be applied to the outer surface of the suction pump 360 to reduce vibration and its associated noise. Suction pump 360 may be contained within its own sub-housing (not shown), which may be formed substantially entirely of molded foam, e.g., used as a silencer to provide sound mitigation by reducing the sound energy of the expelled air during operation of the suction pump 360, and may include a carbon loaded foam. Suction pump 360 provides negative pressure within the chamber 335 of the collection canister 242 by drawing air through the suction port 374.

Pump inlet conduit 372 provides fluid communication between the suction pump 360 and the first filter element 376. The first filter element 376 may include one or more filters and is configured to substantially prevent entry of exudate into the suction pump 360. In embodiments, the control unit 246 stops operation of the suction pump 360 when the first filter element 376 becomes occluded. A variety of filters can be used for the first filter element 376. In one embodiment, the first filter element 376 includes a hydrophobic filter that substantially prevents fluids from entering into the suction pump 360 and potentially causing damage to electronics or pneumatic components. Exhaust air from the pump 360 is vented through an exhaust port (not shown) via the pump outlet conduit 362. Pump outlet conduit 362 may be coupled to one or more filters (not shown) for filtering the exhaust air from the pump 360.

Transducer 340 is in fluid communication with the collection canister 242 to detect the vacuum level within the collection canister 242. In embodiments, the transducer 340 generates an electrical signal that varies as a function of vacuum level within the collection canister 242, and the signal is communicated to the processor 310. Logic associated with the transducer 340 and the pump 360 may reduce the speed of the pump 360 or stop operation of the pump 360 in response to the vacuum level detected by the transducer 340. Any suitable device capable of detecting pressure may be utilized for the transducer 340, including, but not limited to, a pressure switch, transducer or transmitter. Transducer conduit 352 provides fluid communication between the transducer 340 and the second filter element 354. In one embodiment, the second filter element 354 is a hydrophobic filter that substantially prevents fluid contamination of the transducer 340.

First connecting channel 378 provides fluid communication between the first filter element 376 and the suction port 374, when the control unit 246 and the collection canister 242 are operably coupled to each other. Second connecting channel 356 provides fluid communication between the second filter element 354 and the transducer port 396, when the control unit 246 and the collection canister 242 are operably coupled to each other. First connecting channel 378 may be coupled to a control suction port (not shown) located on the bottom side of the control unit 246 and configured to engage with the suction port 374 located on the collection canister top 336 when the control unit 246 and the collection canister 242 are joined together. Second connecting channel 356 may be coupled to a control unit transducer port (not shown) located on the bottom side of the control unit 246 and configured to engage with the transducer port 396 located on the collection canister top 336 when the control unit 246 and the collection canister 242 are joined together.

Control unit 246 also includes a processor 310. In embodiments, the processor 310 is electrically coupled via a transmission line 341 to the transducer 340 and electrically coupled via a transmission line 361 to the suction pump 360. Processor 310 may include any type of computing device, computational circuit, or any type of processor or processing circuit capable of executing a series of instructions that are stored in a memory (not shown) of the control unit 246. The series of instructions may be transmitted via propagated signals for execution by processor 310 for performing the functions described herein and to achieve a technical effect in accordance with the present disclosure. Control unit 246 may also include a user interface (not shown).

Canister assembly 240 also includes a sensor 320. Sensor 320 may include an electrode pair (e.g., 325A, 325B shown in FIG. 4). In embodiments, the sensor 320 is used to measure resistance, capacitance or voltage to provide feedback to the processor 310 indicative of a condition. In embodiments, an electric circuit 328 is electrically coupled via a transmission line 321 between the sensor 320 and the processor 310. Electric circuit 328 is configured to detect an electrical property associated with the sensor 320 and may include various components. Some examples of circuits that may be suitable for use as the electric circuit 328 are illustrated in the circuit diagrams 1401, 1402 and 1403 shown in FIGS. 14A, 14B and 14C, respectively. Although the electric circuit 328 is shown as a separate circuit in FIG. 3, it may be incorporated into the sensor 320, the processor 310, or other component, e.g., a printed circuit board (not shown) associated with the processor 310. Sensor 320 may include multiple electrode pairs (e.g., 325A, 325B and 325C, 3250 shown in FIG. 11). In embodiments, any change in the resistance, capacitance or voltage feedback occurring when the electrodes are simultaneously in contact with exudate in the collection canister 242 is used to indicate a condition, such as, for example, a replace-collection-canister condition or full-collection-canister condition.

Collection canister 242 includes a canister top 336, a chamber 335 to collect wound fluids from the dressing assembly, a suction port 374 to communicate with the chamber 335 and the suction pump 360, a canister inlet port 334 coupled to the extension assembly 230 to introduce the wound fluids from the dressing assembly into the chamber 335, and a transducer port 396 to communicate with the chamber 335 and the transducer 340. Collection canister 242 may be disposable. Canister inlet port 334 may be connectable with the extension assembly 230 by conventional air and fluid tight means, such as those described above. In embodiments, canister inlet port 334 may contain a luer lock or other connector within the purview of those skilled in the art to secure the end of the extension assembly 230 with the canister inlet port 334. Canister inlet port 334 may be configured to receive a cap for use to prevent leakage of exudate and odor from the chamber 335 when the collection canister 242 is separated from the control unit 246.

Figure 4:
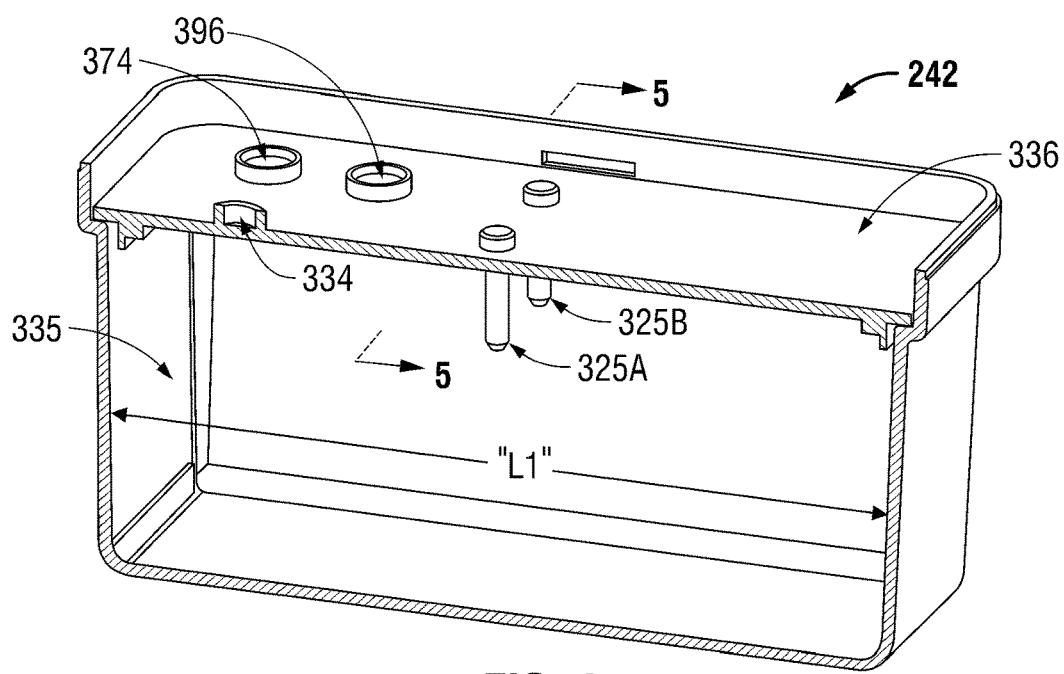
FIG. 4 is a cross-sectional view of the collection canister of the canister assembly shown in FIG. 2 taken along the lines 4-4.

Referring to FIG. 4, an embodiment of the collection canister 242 of the canister assembly 240 illustrated in FIG. 3 is shown and includes the collection canister top 336, the chamber 335, which has length "L1", the canister inlet port 334, the suction port 374, and the transducer port 396. The sensor 320 of FIG. 3 includes is shown as an electrode pair 325A, 325B in FIG. 4. In embodiments, an electric potential (or voltage) is applied to the electrodes 325A, 325B. When a voltage is supplied and the electrodes 325A, 325B are simultaneously in contact with an ionic fluid, e.g., exudate, electric current flows via an electro-chemical reaction that occurs between the ions in the fluid and the electrically polarized electrodes 325A, 325B.

In embodiments, one or more electrode pairs (e.g., 325A, 325B shown in FIG. 4) is coupled to an electric circuit (e.g., 328 shown in FIG. 3), which is configured to detect an electrical properly associated with the electrode pair(s). In embodiments, a measurement of the change in voltage across the electrode pair(s) as a result from the flow of current is used to activate an indicator (e.g., 1358 shown in FIG. 13) as notification to the user of a condition. For example, an indicator may be activated to notify the user that the collection canister 242 is full, which may be referred to as the full-collection-canister condition. An indicator may be activated to notify the user that it is time to replace the collection canister 242, which may be referred to as the replace collection-canister condition. The occurrence of a replace-collection-canister condition does not necessarily indicate that the chamber 335 is full of exudate. Rather, a replace collection-canister condition may indicate that a volume of exudate (less than the volume of the chamber 355) has been collected. User notification of a replace collection-canister condition may thus provide some flexibility to the user in the timing of the replacement or emptying of the collection canister 242, by allowing an additional time period of operation before the volume of the collected exudate reaches the maximum volume capacity of the chamber 355.

Figure 5:
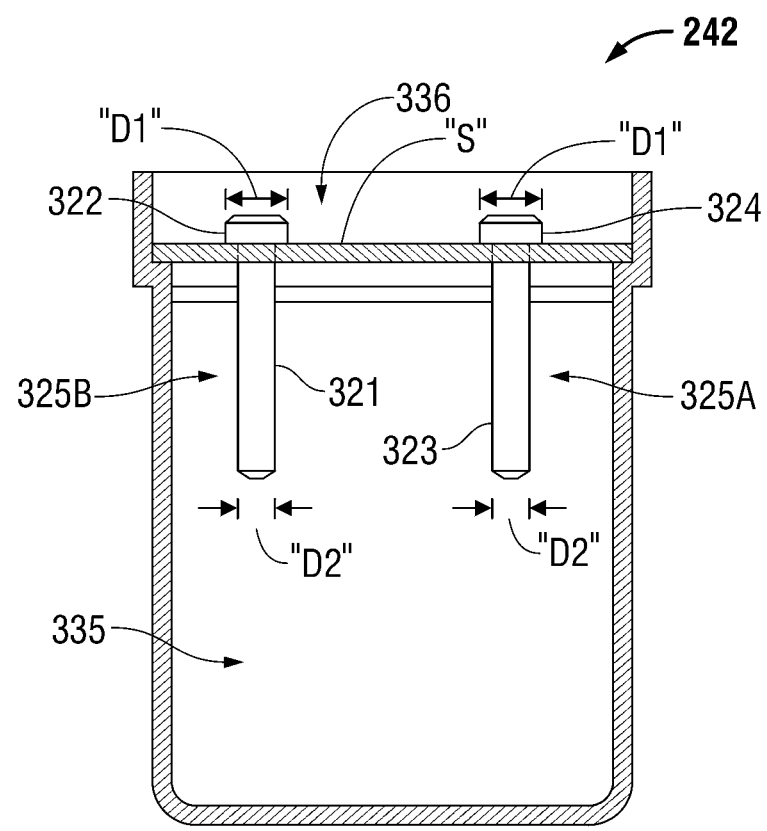
FIG. 5 is a cross-sectional view of the collection canister shown in FIG. 4 taken along the lines 5-5.

Referring to FIG. 5, a cross-sectional view of the collection canister 242 illustrated in FIG. 4 is shown and includes the collection canister top 336, the chamber 335, and the two electrodes 325A, 325B. Electrodes 325A, 325B include a first portion 322, 324 and a second portion 321, 323, respectively, wherein the first portions 322, 324 have a first diameter "D1" and the second portions 321, 323 have a second diameter "D2", which is smaller than the first diameter "D1". In an embodiment, the first portions 322, 324 are supported by the surface "S" of the collection canister top 336. In an alternative embodiment, the first portions 322, 324 are arranged to be substantially flush with the surface "S" of the collection canister top 336. Each of the second portions 321, 323 extends downwardly from the collection canister top 336 through a corresponding hole in the collection canister top 336 and into the chamber 335. Electrodes 325A, 325B, or portions thereof, include electrically conductive material, e.g., metal or metal alloy. Electrodes 325A, 325B, or portions thereof, may include an electrically conductive coating. For example, electrodes 325A, 325B, or portions thereof, may be plated with an electrically conductive metallic layer. The relative positions, size and/or shape of the two electrodes 325A, 325B may be varied from an embodiment depicted in FIG. 5.

In embodiments, two probe contacts (not shown) are located at the bottom side of the control unit 246 and positioned to make electrical contact with the first portions 322, 324 of the electrodes 325A, 325B, respectively, when the collection canister 242 and the control unit 246 are connected to each other.

Figure 6:
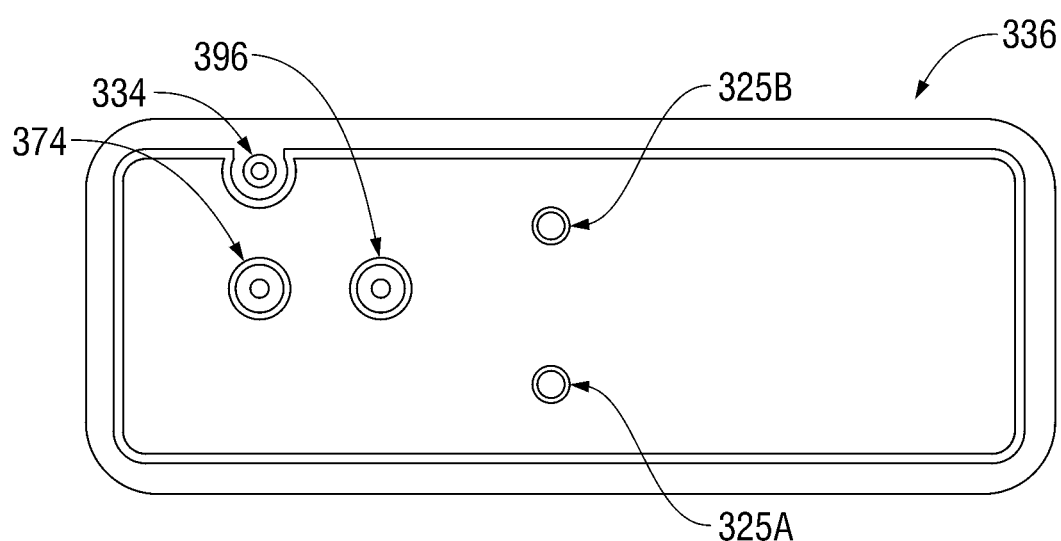
FIG. 6 is a bottom view of the collection canister top shown in FIG. 4.

FIG. 6 is a bottom view of the collection canister top 336 illustrated in FIG. 4 shown with the canister inlet port 334, the suction port 374, the transducer port 396 and the two electrodes 325A, 325B. The relative positions, size and/or shape of the canister inlet port 334, the suction port 374 and the transducer port 396 may be varied from an embodiment depicted in FIGS. 4 and 6.

Figure 7:
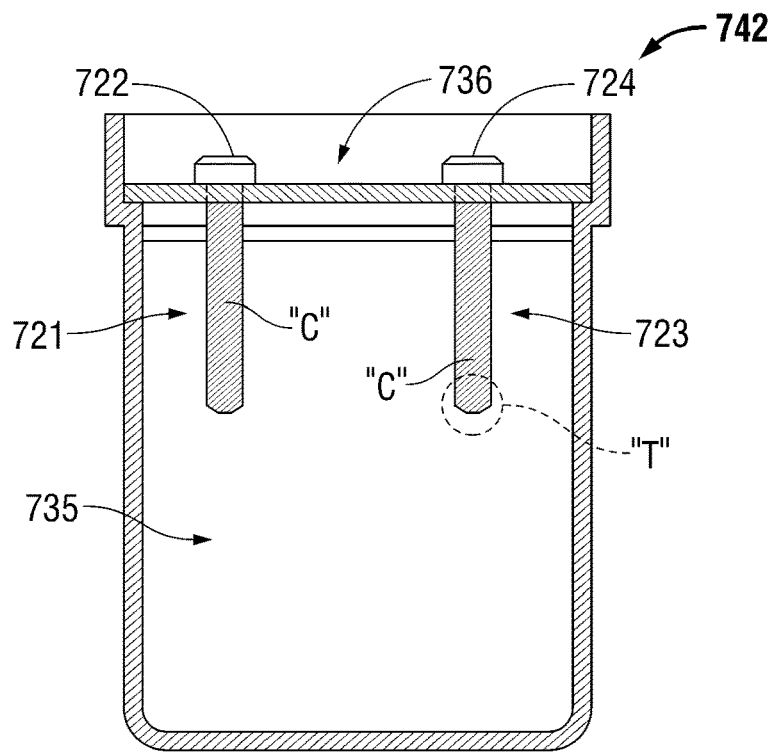
FIG. 7 is a cross-sectional view of another embodiment of a collection canister in accordance with the present disclosure.

Referring to FIG. 7, an embodiment of a collection canister 742 is shown and includes a collection canister top 736 and a chamber 735. Collection canister 742 is similar to the collection canister 242 illustrated in FIGS. 4 and 5. Collection canister 742 includes two electrodes with a first portion 722, 724 and a second portion 721, 723, respectively, which are similar to the two electrodes 325A, 325B shown in FIG. 4, except that the second portions 721, 723 of FIG. 7 are substantially covered by a coating "C". In alternative embodiments, coating "C" covers a section of the second portions 721, 723, such as the tip section "T".

In embodiments, the coating "C" is a water-soluble coating for the protection of the second portions 721, 723 and may have a predetermined amount of time in contact with fluid before the coating dissolves. Coating "C" may inhibit encrustation of the second portions 721, 723 formed by the drying of exudate. For example, the coating "C" may inhibit encrustation by affecting the formation and binding of proteins or may decrease wetability of the second portions 721, 723 and allow liquid to shed.

Coating "C" may help to minimize the amount of time that fluid in the chamber 735 of the collection canister 742 comes into contact with the second portions 721,723, e.g., during accidental tip over of the canister assembly (e.g., 240 shown in FIG. 12) or during ambulation while the canister assembly is worn or carried by the user. In embodiments, the coating "C" is characterized by a predetermined amount of time in contact with fluid before the coating "C" dissolves. The predetermined amount of time may be a short period of time, e.g., about one hour to about ten hours, which may be suitable in the case of a high rate of flow of exudate from the wound into the chamber 735. The predetermined amount of time may be a long period of time, e.g., about forty-eight hours, which may be suitable in the case of a low rate of flow of exudate into the chamber 735. The predetermined amount of time in contact with fluid before the coating "C" dissolves may be varied from the above-mentioned time periods. In some cases, depending on characteristics of the fluid to be collected in the collection canister 742, the coating "C" may be configured to dissolve at a predetermined rate, e.g., based on the thickness, density and/or composition of the coating "C".

Figure 8:
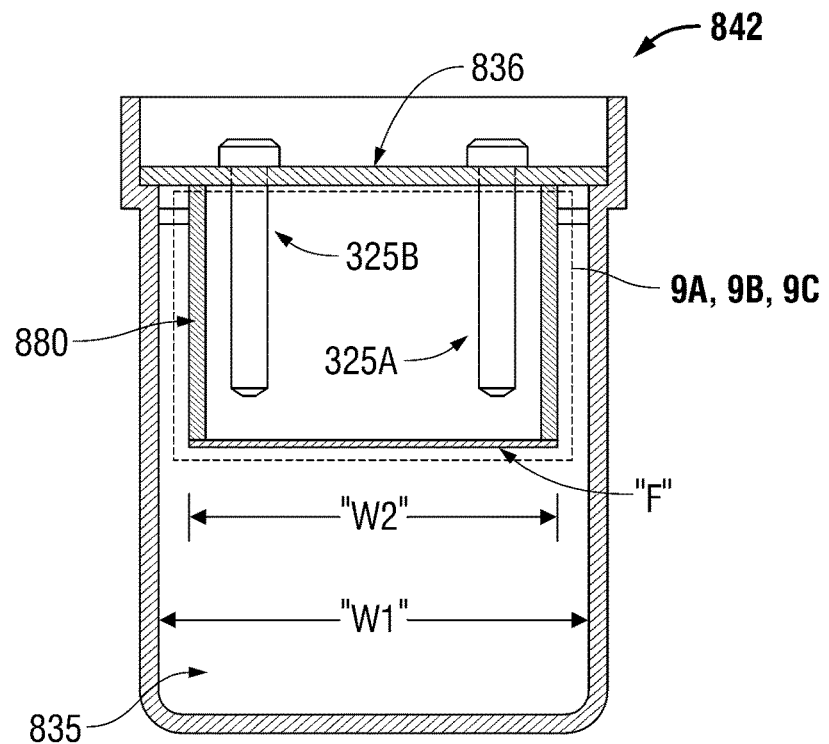
FIG. 8 is a cross-sectional view of yet another embodiment of a collection canister in accordance with the present disclosure.

Referring to FIG. 8, an embodiment of a collection canister 842 is shown and includes a collection canister top 836 and a fluid collection chamber 835 having a width "W1". Collection canister 842 also includes the two electrodes 325A, 325B shown in FIGS. 4 and 5. Collection canister 842 is similar to the collection canister 242 illustrated in FIGS. 4 and 5, except that the two electrodes 325A, 325B are disposed within an electrical contact protection unit bounded by the collection canister top 836, an inner wall 880 and a bottom end "F". The electrical contact protection unit may be formed in various sizes and shapes, such as, for example, the shapes shown in FIGS. 9A, 9B and 9C.

In embodiments, the bottom end "F", or portion thereof, is formed of a water soluble film, which is configured to dissolve over a period of time. In embodiments, the water soluble film dissolves over a period of time depending on characteristics of the water soluble film, e.g., thickness, density and/or composition of the water soluble film, characteristics of the fluid contained in the fluid collection chamber, e.g., pH, viscosity and/or ionic composition of the fluid, and/or the rate of flow of the fluid into the fluid collection chamber 835.

Figure 9A:
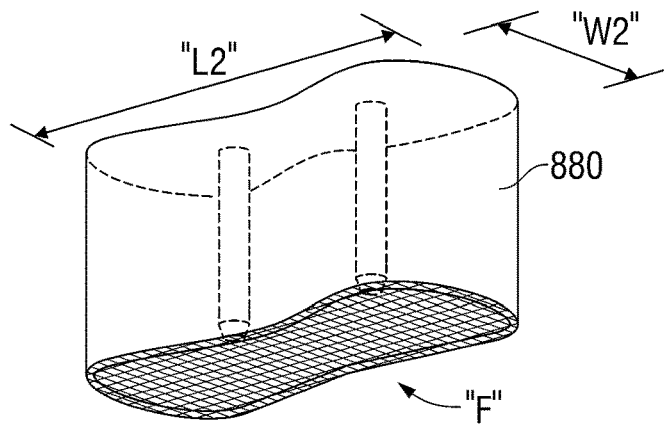
FIGS. 9A through 9C are perspective views of embodiments of the electrical contact protection unit of the collection canister illustrated in FIG. 8, shown with varied geometric shapes, in accordance with the present disclosure.
Figure 9B:
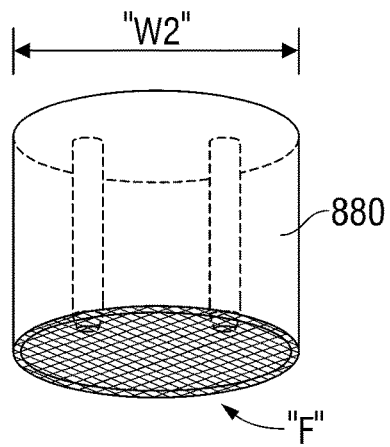
Figure 9C:
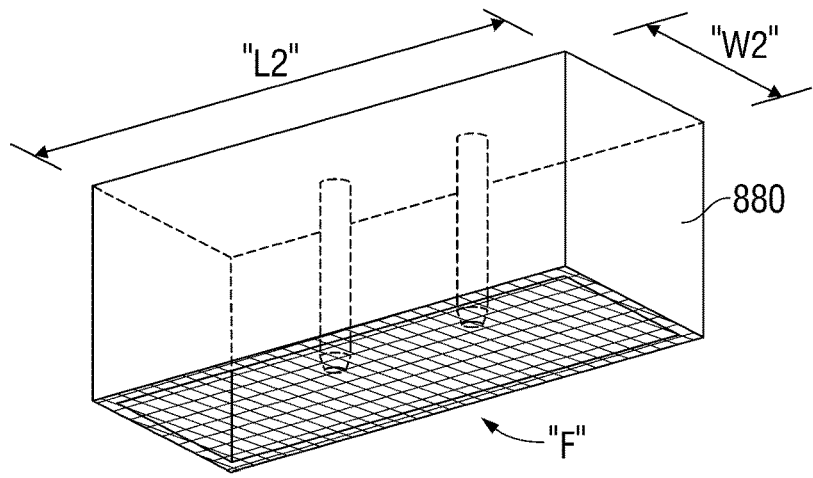

Referring to FIGS. 9A through 9C, embodiments of the electrical contact protection unit of the collection canister 842 illustrated in FIG. 8 are shown with varied geometric shapes. Each of the electrical contact protection units shown in FIGS. 9A through 9C includes an inner wall 880 and a bottom end "F", and each has a width (or maximum width) "W2" that is less than the width "W1" of the fluid collection chamber 835 shown in FIG. 8. The electrical contact protection units shown in FIGS. 9A and 9C have a length "L2", which is less than the length "L1" of the chamber 335 of the canister 242 shown in FIGS. 4 and 5. The relative positions, size and/or shape of the electrical contact protection units may be varied from embodiments depicted in FIGS. 8 through 9C.

Figure 10:
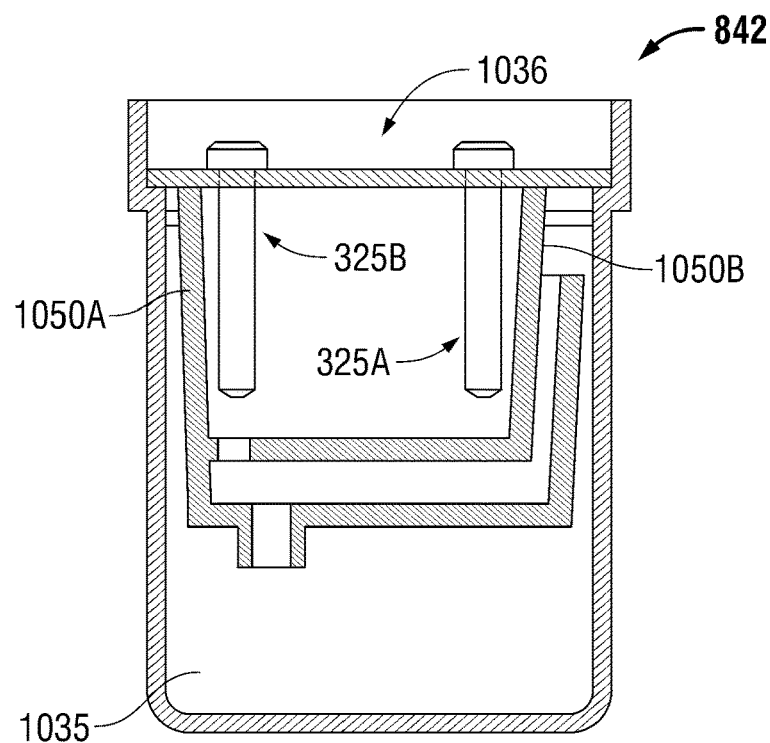
FIG. 10 is a schematic diagram of another embodiment of a collection canister in accordance with the present disclosure.

Referring to FIG. 10, an embodiment of a collection canister 1042 is shown and includes a collection canister top 1036 and a chamber 1035. Collection canister 1042 also includes the two electrodes 325A, 325B shown in FIGS. 4 and 5. Collection canister 1042 is similar to the collection canister 242 illustrated in FIGS. 4 and 5, except that the two electrodes 325A, 325B are disposed within a baffle unit formed of two baffle members 1050A, 1050B. Baffle members 1050A, 1050B may be formed in various sizes and shapes.

Figure 11:
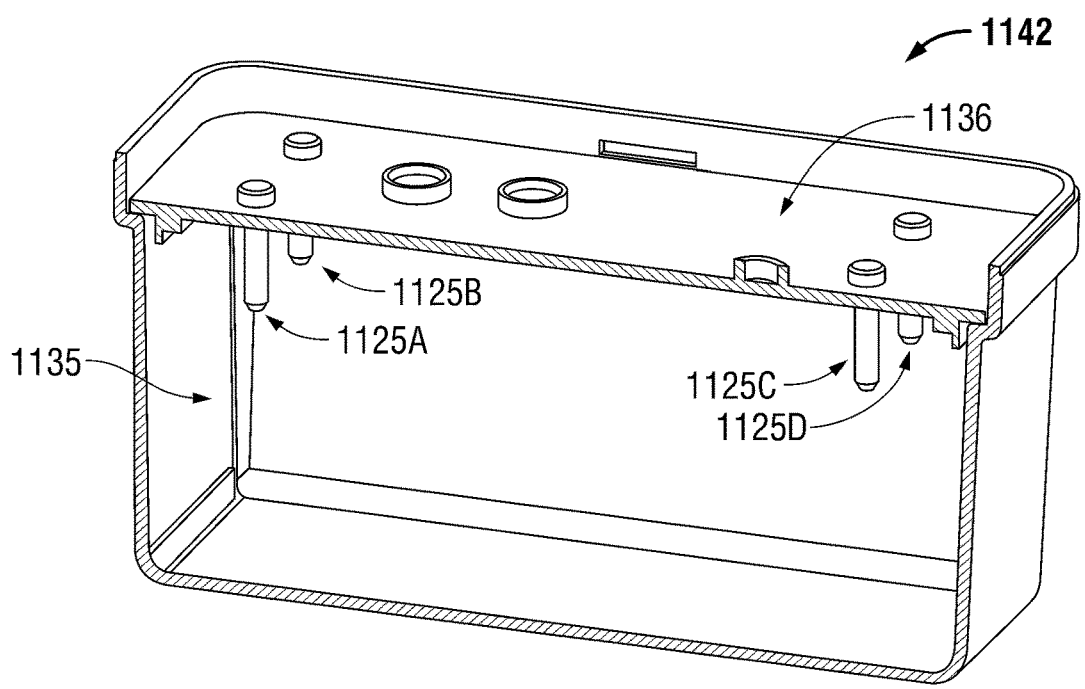
FIG. 11 is a cross-sectional view of yet another embodiment of a collection canister in accordance with the present disclosure.

Referring to FIG. 11, an embodiment of a collection canister 1142 is shown and includes a collection canister top 1136, a chamber 1135, a first electrode pair 1125A, 1125B and a second electrode pair 1125C, 1125D. In one embodiment, a measurement of the change in voltage across the first electrode pair 1125A, 1125B is used to activate an indicator as notification to the user of a replace-collection-canister condition, and a measurement of the change in voltage across the second electrode pair 1125C, 1125D is used to activate an indicator as notification to the user of a full collection canister condition.

Figure 12:
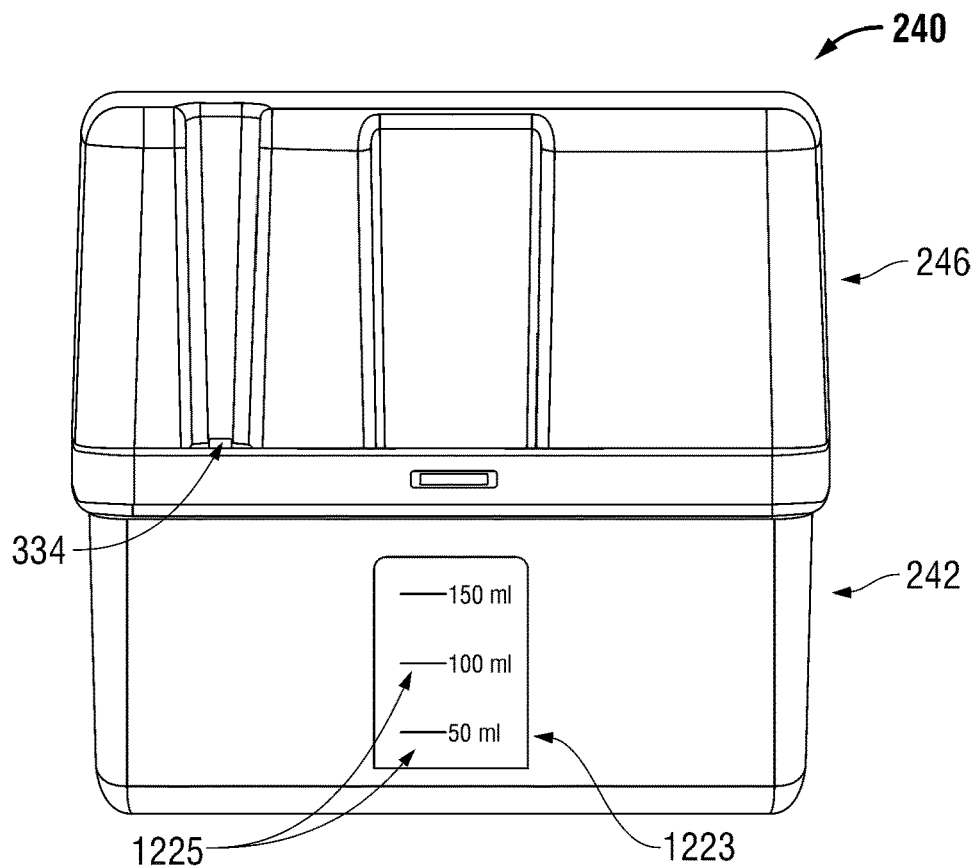
FIG. 12 is a perspective view of the canister assembly of the negative pressure wound therapy system illustrated in FIG. 2 shown with a window having fluid level markings in accordance with the present disclosure.

Referring to FIG. 12, the canister assembly 240 of the negative pressure wound therapy system illustrated in FIG. 2 is shown and includes the collection canister 242 shown with a transparent or semi-transparent portion 1223. Transparent or semi-transparent portion 1223 includes fluid level markings or graduations 1225 and may help to permit a visual assessment of the amount of exudate contained within the collection canister 242, and, thus, may assist in determining the remaining capacity of the collection canister 242 and/or when the collection canister 242 should be replaced or emptied. Transparent or semi-transparent portion 1223 may help to permit a visual assessment of the wound exudate to assist in evaluating the color, quality and/or quantity of exudate.

Figure 13:
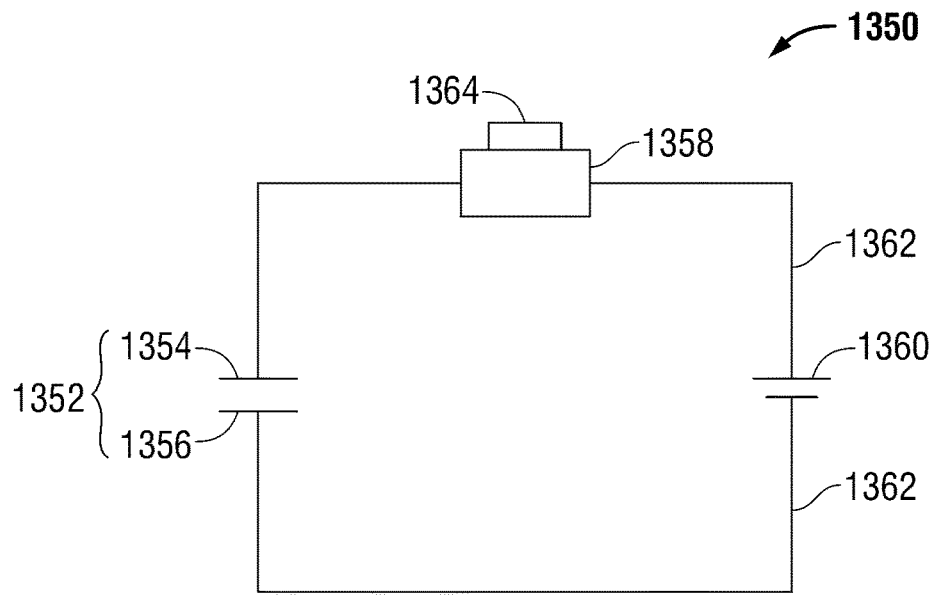
FIG. 13 is a schematic diagram of an embodiment of a detector circuit in accordance with the present disclosure.

Referring to FIG. 13, an embodiment of a detector circuit 1350 is shown and includes a sensor 1352, incorporating electrically conductive contacts 1354 and 1356, and indicator unit 1358. Contacts 1534 and 1356 may be disposed within the collection canister 242 at a pre-determined height or level within the collection canister 242 corresponding to a targeted volume of fluid or exudate accumulated within the collection canister 242. For example, contacts 1354 and 1356 may be positioned within the collection canister 242 at a position corresponding to the maximum fill volume of collection canister 122.

As illustrated in FIG. 13, contacts 1354 and 1356 of sensor 1352 are laterally spaced. Contacts 1354 and 1356 are connected via transmission lines 1362 to the indicator unit 1352 and power source 1360. Alkaline batteries, wet cell batteries, dry cell batteries, nickel cadmium batteries, lithium batteries, NiMH batteries (nickel metal hydride), solar energy and other energy sources may serve as the power 1360. Power source 1360 may be a separate unit from the power source utilized to energize the vacuum source (e.g., 360 shown in FIG. 3).

In embodiments, the indicator unit 1358 of the detector circuit 1350 generates an alert or signal that the canister 242 is full of a fluid, e.g., exudate. Indicator unit 1358 may be any type of indicator capable of alerting the user or clinician that the canister 242 needs to be replaced. Indicator unit 1358 may be an audio and/or visual indicator. In an embodiment, the indicator unit 1358 includes an alarm or output component 1364, which includes logic or circuitry to generate a signal when power is provided to the indicator unit 1358. Output component 164 is adapted to provide a perceptible sensory alert, which may be an audio, visual, or other sensory alarm. In one embodiment, the indicator 1358 is adapted to generate an audio signal and the output component 1364 includes an audio circuit with a speaker. In one embodiment, the indicator 1358 is adapted to generate a visual signal and the output component 1364 includes a light source, such as a light-emitting diode (LED).

Figure 14A:
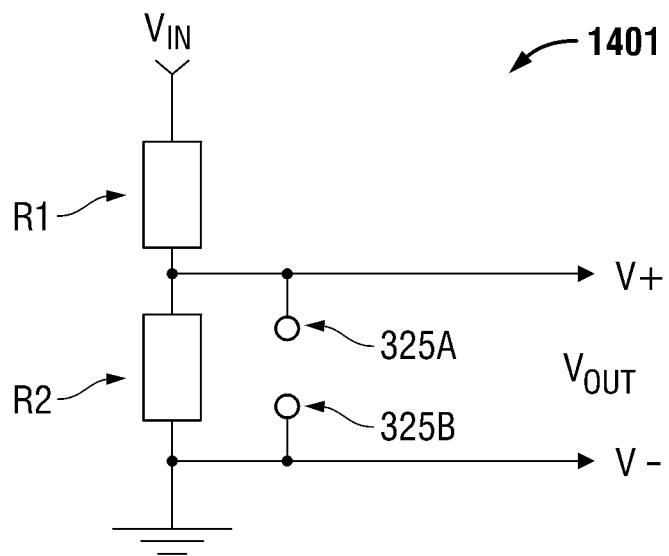
FIG. 14A is a schematic diagram of an embodiment of a detection circuit in accordance with the present disclosure.
Figure 14B:
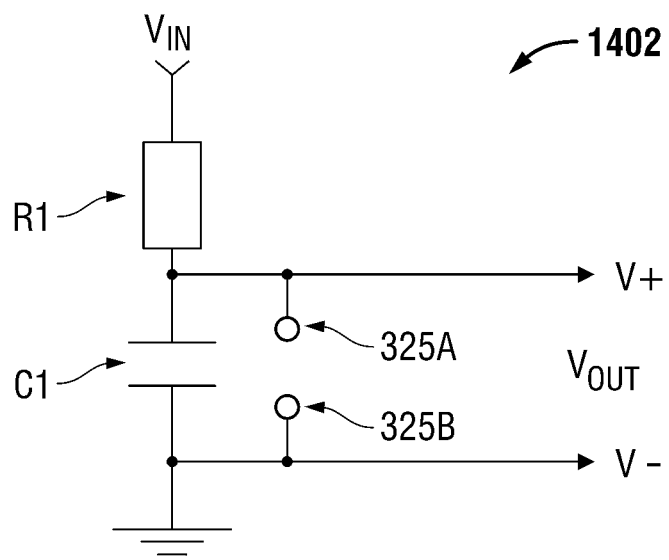
FIG. 14B is a schematic diagram of another embodiment of a detection circuit in accordance with the present disclosure.

FIGS. 14A and 14B are schematic diagrams of detection circuits 1401, 1402, respectively, for use to detect a voltage measurement across an electrode pair, e.g., the electrodes 325A, 325B shown in FIGS. 4 and 5. Detection circuit 1401 includes a first resistor R1 and a second resistor R2. In an embodiment, wherein the first resistor R1 is a 10000000 ohm (10000K or 10M) resistor, the second resistor R2 is a 24M ohm resistor, and V1N equals 3.3V, the detection circuit 1401 may produce a constant 2.4V output (VOUT) when no exudate has shorted the two electrodes 325A, 325B.

Referring to FIG. 14B, the detection circuit 1402 includes a resistor R1 and a capacitor C1. In an embodiment, wherein the resistor R1 is a 100000 ohm (100K) resistor, the capacitor C1 is a 100 pf capacitor, and $V_{IN}$ equals 3.3V, the detection circuit 1402 may produce a constant 3.3V output ($V_{OUT}$) when no exudate has shorted the two electrodes 325A, 325B.

In the detection circuits 1401 and 1402, when the two electrodes 325A, 325B make contact with an ionic fluid, e.g., exudate, electric current flows via an electrochemical reaction that occurs between the ions in the fluid and the electrically polarized electrodes 325A, 325B, resulting in a change in the measured voltage output ($V_{OUT}$). In embodiments, a measurement of the change in voltage across the electrode pair(s) as a result from the flow of current is used to activate an indicator (e.g., 1358 shown in FIG. 13) as notification to the user to replace or empty the collection canister (e.g., 242 shown in FIGS. 4 and 5).

Although embodiments of the present disclosure have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A negative pressure wound therapy system, comprising:
   a collection canister comprising a chamber configured to collect wound fluids, the collection canister comprising a top surface;
   a control unit comprising an enclosure enclosing a vacuum source and a controller, the enclosure including a bottom surface, wherein the top surface of the collection canister and the bottom surface of the control unit are configured to be removably coupled; and
   a sensor positioned at least partially on the top surface of the collection canister, the sensor configured to be electrically connected with a probe positioned on the bottom side of the enclosure when the collection canister and the control unit are coupled,
   wherein the sensor comprises at least one electrode at least partially extending into the chamber;
   wherein the at least one electrode is configured to communicate with the controller; and
   wherein the vacuum source is configured to deliver negative pressure to a wound covered by a dressing when the collection canister and control unit are coupled.

2. The negative pressure wound therapy system of claim 1, further comprising a circuit configured to be electrically connected with the sensor and the probe.

3. The negative pressure wound therapy system of claim 1, further comprising a circuit configured to detect a change in the electrical property associated with the sensor, wherein the change in the electrical property comprises a change in at least one of resistance, capacitance, or voltage.

4. The negative pressure wound therapy system of claim 1, wherein the at least one electrode comprises:
   a first electrode including a first portion and a second portion, wherein the first portion of the first electrode is supported by the top surface of the collection canister, and the second portion of the first electrode extends into the chamber; and
   a second electrode including a first portion and a second portion, wherein the first portion of the second electrode is supported by the top surface of the collection canister, and the second portion of the second electrode extends into the chamber;
   wherein the controller is configured to, based on a change in an electrical property associated with the first and second electrodes, indicate a condition associated with the collection canister.

5. The negative pressure wound therapy system of claim 4, wherein the condition associated with the collection canister comprises collecting a particular volume of fluid in the collection canister, and wherein the controller is configured to indicate the condition based on the first and second electrodes being simultaneously in contact with fluid in the collection canister.

6. A negative pressure wound therapy system, comprising:
   a collection canister comprising a chamber configured to collect wound fluids, the collection canister comprising a first surface;
   an enclosure enclosing a vacuum source and a controller, the enclosure including a second surface, wherein the first surface of the collection canister and the second surface are configured to be removably coupled; and
   a sensor configured to detect a condition associated with the collection canister, the sensor comprising:
      a first electrode including a first portion and a second portion, wherein the first portion of the first electrode is supported by the first surface of the collection canister, and the second portion of the first electrode extends into the chamber;
      a second electrode including a first portion and a second portion, wherein the first portion of the second electrode is supported by the first surface of the collection canister, and the second portion of the second electrode extends into the chamber;
   wherein a change in resistance, capacitance, or voltage in the first and second electrodes indicates the condition associated with the collection canister;
   wherein the first portions of the first and second electrodes comprise a first diameter and a rounded end and the second portions of the first and second electrodes comprise a second diameter and a cylindrical shape, wherein the first diameter is larger than the second diameter; and
   wherein the first portions of the first and second electrodes are substantially flush with the first surface of the collection canister allowing for coupling of the enclosure to the collection canister.

7. The negative pressure wound therapy system of claim 6, wherein the first portions of the first and second electrodes on the first surface of the collection canister are configured to be in electrical contact with one or more probes on the second surface of the enclosure when the collection canister and the enclosure are coupled.

8. The negative pressure wound therapy system of claim 6, further comprising an inner wall disposed within the chamber, wherein the second portions of the first and second electrodes are disposed within an area between a top portion of the collection canister and the inner wall.

9. The negative pressure wound therapy system of claim 8, wherein the inner wall is configured to:
   deflect the wound fluid from contacting the first and second electrodes when the collection canister is tilted, and allow the wound fluid to contact the first and second electrodes when the chamber is substantially full.

10. The negative pressure wound therapy system of claim 8, wherein the inner wall is integral to and not removable from the chamber.

11. The negative pressure wound therapy system of claim 8, wherein the area between the top portion of the collection canister and the inner wall is configured to be filled with the wound fluid when the collection canister is substantially full with the wound fluid.

12. The negative pressure wound therapy system of claim 6, wherein the controller is configured to monitor and control a negative pressure within the collection canister.

13. The negative pressure wound therapy system of claim 6, wherein the condition in the collection canister comprises a replace-collection-canister condition or a full-collection-canister condition.

* * * * *